United States Patent
Sahoo et al.

(10) Patent No.: US 6,645,997 B2
(45) Date of Patent: Nov. 11, 2003

(54) BENZOPYRANCARBOXYLIC ACID DERIVATIVES FOR THE TREATMENT OF DIABETES AND LIPID DISORDERS

(75) Inventors: Soumya P. Sahoo, Old Bridge, NJ (US); Hiroo Koyama, Hoboken, NJ (US); Daniel J. Miller, Edison, NJ (US); Julia K. Boueres, Piscataway, NJ (US); Ranjit C. Desai, Kendall Park, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/961,841

(22) Filed: Sep. 24, 2001

(65) Prior Publication Data

US 2002/0082292 A1 Jun. 27, 2002

Related U.S. Application Data

(60) Provisional application No. 60/235,708, filed on Sep. 27, 2000, and provisional application No. 60/244,697, filed on Oct. 31, 2000.

(51) Int. Cl.[7] .................. A01N 43/16; C07D 311/04; C07D 311/74; C07D 311/76
(52) U.S. Cl. ............... 514/456; 514/457; 549/399; 549/400; 549/401; 549/402; 549/404; 549/405
(58) Field of Search ............... 549/405, 401, 549/402, 400, 399, 404; 514/456, 457

(56) References Cited

U.S. PATENT DOCUMENTS

| | | | | |
|---|---|---|---|---|
| 4,680,404 A | * | 7/1987 | Eggler et al. | 549/401 |
| 4,778,903 A | * | 10/1988 | Miyano et al. | 549/405 |
| 4,885,309 A | | 12/1989 | Welton | |
| 4,889,871 A | * | 12/1989 | Djuric et al. | 549/401 |
| 5,003,090 A | * | 3/1991 | Manchamd et al. | 549/405 |
| 5,073,562 A | | 12/1991 | Djuric et al. | |
| 5,112,856 A | | 5/1992 | Gaginella et al. | |
| 5,324,743 A | | 6/1994 | Dillard et al. | |
| 5,352,690 A | | 10/1994 | Sofia | |
| 5,439,937 A | | 8/1995 | Djuric et al. | |

FOREIGN PATENT DOCUMENTS

| | | |
|---|---|---|
| EP | 0079637 | 5/1983 |
| EP | 0129906 | 1/1985 |
| EP | 0139809 | 5/1985 |
| EP | 0150447 | 8/1985 |
| EP | 0336068 | 10/1989 |
| EP | 0743064 | 11/1996 |
| EP | 0 801 060 A1 | 10/1997 |
| WO | WO 95/17183 | 6/1995 |
| WO | WO 96/06604 | 3/1996 |
| WO | WO 00/12086 | 3/2000 |
| WO | WO 00/16798 | 3/2000 |

OTHER PUBLICATIONS

Gerald M. Reaven: "Role of Insulin Resistance in Human Disease", Diabetes, vol. 37, Dec. 1988, pp. 1595–1607.
Koji Murakami, et al. "A Novel Insulin Sensitizer Acts as a Coligand for Peroxisome Proliferator–Activated Receptor..," Diabetes, vol. 47, 1998, pp. 1841–1847.
"2002 Published USAN", at http://www.ama–assn.org/.
"2001 Published USAN", at http://www.ama–assn.org/.
Noal Cohen, et al., J. Med. Chem., 1989, vol. 32., pp. 1842–1860.
Noal Cohen, et al., Bioorganic & Medicinal Chemistry Letters, 1994, vol. 4, No. 24., pp. 2883–2888.
Stevan W. Djuric, et al., Bioorganic & Medicinal Chemistry Letters, 1994, vol. 4, No. 6., pp. 811–816.
Richard W. Harper, et al., J. Med. Chem., 1994, vol. 37, pp. 2411–2420.
William T. Jackson, et al., The Journal of Pharmacology and Experimental Therapeutics, 1999, vol. 288, pp. 286–294.
Thomas D. Penning, et al., J. Med. Chem., 1995, vol. 38., pp. 858–868.
J. Scott Sawyer, et al., J. Med. Chem., 1995, vol. 38, pp. 4411–4432.
Michael J. Sofia, et al., Bioorganic & Medicinal Chemistry, 1992, vol. 2, No. 12, pp. 1675–1680.

* cited by examiner

Primary Examiner—Alan L. Rotman
Assistant Examiner—Raymond Covington
(74) Attorney, Agent, or Firm—James L. McGinnis; Melvin Winokur

(57) ABSTRACT

A class of benzopyrancarboxylic acid derivatives comprises compounds that are potent agonists of PPAR alpha and/or gamma, and are therefore useful in the treatment, control or prevention of non-insulin dependent diabetes mellitus (NIDDM), hyperglycemia, dyslipidemia, hyperlipidemia, hypercholesterolemia, hypertriglyceridemia, atherosclerosis, obesity, vascular restenosis, inflammation, and other PPAR alpha and/or gamma mediated diseases, disorders and conditions.

45 Claims, No Drawings

BENZOPYRANCARBOXYLIC ACID DERIVATIVES FOR THE TREATMENT OF DIABETES AND LIPID DISORDERS

CROSS REFERENCE TO RELATED APPLICATIONS

This application claims priority from U.S. Provisional Applications No. 60/235,708, filed on Sep. 27, 2000, and 60/244,697 filed on Oct. 31, 2000, which are incorporated by reference into this application in their entirety.

FIELD OF THE INVENTION

The instant invention is concerned with benzopyrancarboxylic acids and related heterocyclic compounds and pharmaceutically acceptable salts and prodrugs thereof which are useful as therapeutic compounds, particularly in the treatment and prevention of Type 2 diabetes mellitus, often referred to as non-insulin dependent diabetes (NIDDM), of conditions that are often associated with this disease, and of lipid disorders.

BACKGROUND OF THE INVENTION

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide), which stimulate the pancreatic β-cells to secrete more insulin, and/or by injection of insulin after the response to sulfonylureas fails, will result in high enough insulin concentrations to stimulate the very insulin-resistant tissues. However, dangerously low levels of plasma glucose can result from these last two treatments, and increasing insulin resistance due to the even higher plasma insulin levels can occur. The biguanides increase insulin sensitivity resulting in some correction of hyperglycemia. However, the two biguanides, phenformin and metformin, can induce lactic acidosis and nausea/diarrhea, respectively.

The glitazones (i.e. 5-benzylthiazolidine-2,4-diones) are a more recently described class of compounds with potential for a novel mode of action in ameliorating many symptoms of type 2 diabetes. These agents substantially increase insulin sensitivity in muscle, liver and adipose tissue in several animal models of type 2 diabetes resulting in partial or complete correction of the elevated plasma levels of glucose without occurrence of hypoglycemia. For a review, see Willson, T. M. et al., *J. Med. Chem.* 43(4) 527–550, (2000).

Disorders of lipid metabolism or dyslipidemias include various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as Low Density Lipoproteins (LDL), Very Low Density Lipoproteins (VLDL) and Intermediate Density Lipoproteins (IDL). Cholesterol is mostly carried in Low Density Lipoproteins (LDL), and this component is commonly known as the "bad" cholesterol because it has been shown that elevations in IDL-cholesterol correlate closely to the risk of coronary heart disease. A smaller component of cholesterol is carried in the High Density Lipoproteins (HDL) and is commonly known as the "good" cholesterol. In fact, it is known that the primary function of HDL is to accept cholesterol deposited in the arterial wall and to transport it back to the liver for disposal through the intestine. Although it is desirable to lower elevated levels of LDL cholesterol, it is also desirable to increase levels of HDL cholesterol. Generally, it has been found that increased levels of HDL are associated with lower risk for coronary heart disease (CHD). See, for example, Gordon, et al., Am. J. Med., 62, 707–714 (1977); Stampfer, et al., N. England J. Med., 325, 373–381 (1991); and Kannel, et al., Ann. Internal Med., 90, 85–91 (1979). An example of an HDL raising agent is nicotinic acid, a drug with limited utility because doses that achieve HDL raising are associated with undesirable effects, such as flushing.

Dyslipidemias were originally classified by Fredrickson according to the combination of alterations mentioned above. The Fredrickson classification includes 6 phenotypes (i.e., I, IIa, IIb, III, IV and V) with the most common being the isolated hypercholesterolemia (or type IIa) which is usually accompained by elevated concentrations of total and LDL cholesterol. The initial treatment for hypercholesterolemia is often to modify the diet to one low in fat and cholesterol, coupled with appropriate physical exercise, followed by drug therapy when IDL-lowering goals are not met by diet and exercise alone A second common form of dyslipidemia is the mixed or combined hyperlipidemia or type IIb and III of the Fredrickson classification. This dyslipidemia is often prevalent in patients with type 2 diabetes, obesity and the metabolic syndrome. In this dyslipidemia there are modest elevations of LDL-cholesterol, accompanied by more pronounced elevations of small dense LDL-cholesterol particles, VIDL and/or IDL (i.e., triglyceride rich lipoproteins), and total triglycerides. In addition, concentrations of HDL are often low.

Peroxisome proliferators are a structurally diverse group of compounds that when administered to rodents elicit dramatic increases in the size and number of hepatic and renal peroxisomes, as well as concomitant increases in the capacity of peroxisomes to metabolize fatty acids via increased expression of the enzymes of the beta-oxidation cycle. Compounds of this group include but are not limited to the fibrate class of lipid modulating drugs, herbicides and phthalate plasticizers. Peroxisome proliferation is also triggered by dietary or physiological factors such as a high-fat diet and cold acclimatization.

Three sub-types of peroxisome proliferator activated receptor (PPAR) have been discovered and described; they are peroxisome proliferator activated receptor alpha (PPARα), peroxisome proliferator activated receptor gamma (PPARγ) and peroxisome proliferator activated receptor delta (PPARδ). Identification of PPARα, a member of the nuclear hormone receptor superfamily activated by peroxisome proliferators, has facilitated analysis of the mechanism by which peroxisome proliferators exert their pleiotropic effects. PPARα is activated by a number of medium and long-chain fatty acids, and it is involved in stimulating β-oxidation of fatty acids. PPARα is also associated with the activity of fibrates and fatty acids in rodents and humans. Fibric acid derivatives such as clofibrate, fenofibrate, bezafibrate, ciprofibrate, beclofibrate and etofibrate, as well as gemfibrozil, each of which are PPARα ligands and/or activators, produce a substantial reduction in plasma triglycerides as well as some increase in HDL. The effects on LDL cholesterol are inconsistent and might depend upon the compound and/or the dyslipidemic phenotype. For these reasons, this class of compounds has been primarily used to treat hypertriglyceridemia (i.e., Fredrickson Type IV and V) and/or mixed hyperlipidemia.

The PPARγ receptor subtypes are involved in activating the program of adipocyte differentiation and are not involved in stimulating peroxisome proliferation in the liver. There are two known protein isoforms of PPARγ: PPARγ1 and PPARγ2 which differ only in that PPARγ2 contains an additional 28 amino acids present at the amino terminus. The DNA sequences for the human isotypes are described in Elbrecht, et al., BBRC 224;431–437 (1996). In mice, PPARγ2 is expressed specifically in fat cells. Tontonoz et al., *Cell* 79: 1147–1156 (1994) provide evidence to show that one physiological role of PPARγ is to induce adipocyte differentiation. As with other members of the nuclear hormone receptor superfamily, PPARγ2 regulates the expression of genes through interaction with other proteins and binding to hormone response elements, for example in the 5' flanking regions of responsive genes. An example of a PPARγ2 responsive gene is the tissue-specific adipocyte P2 gene. Although peroxisome proliferators, including the fibrates and fatty acids, activate the transcriptional activity of PPAR's, only prostaglandin J$_2$ derivatives have been identified as potential natural ligands of the PPARγ subtype, which also binds thiazolidinedione antidiabetic agents with high affinity.

The human nuclear receptor gene PPARδ (hPPARδ) has been cloned from a human osteosarcoma cell cDNA library and is fully described in A. Schmidt et al., *Molecular Endocrinology*, 6:1634–1641 (1992). It should be noted that PPARδ is also referred to in the literature as PPARβ and as NUC1, and each of these names refers to the same receptor; in Schmidt et al. the receptor is referred to as NUC1.

In WO96/01430, a human PPAR subtype, hNUC1B, is disclosed. The amino acid sequence of hNUC1B differs from human PPARδ (referred to therein as hNUC1) by one amino acid, i.e., alanine at position 292. Based on in vivo experiments described therein, the authors suggest that hNUC1B protein represses hPPARα and thyroid hormone receptor protein activity.

It has been disclosed in WO97/28149 that agonists of PPARδ are useful in raising HDL plasma levels. WO97/27857, 97/28115, 97/28137 and 97/27847 disclose compounds that are useful as antidiabetic, antiobesity, antiatherosclerosis and antihyperlipidemic agents, and which may exert their effect through activation of PPARs.

It is generally believed that glitazones exert their effects by binding to the peroxisome proliferator activated receptor (PPAR) family of receptors, controlling certain transcription elements having to do with the biological entities listed above. See Hulin et al., Current Pharm. Design (1996) 2, 85–102.

A number of glitazones that are PPAR agonists have been approved for use in the treatment of diabetes. These include troglitazone, rosiglitazone and pioglitazone, all of which are primarily or exclusively PPARγ agonists. Many of the newer PPAR agonists that are currently under development or are in clinical trials have dual PPARα and γ activity. These are expected to improve both insulin sensitivity and the lipid profile in patients having NIDDM.

Although glitazones are beneficial in the treatment of NIDDM, there have been some serious adverse events associated with the use of the compounds. The most serious of these has been liver toxicity, which has resulted in a number of deaths. The most serious problems have occurred using troglitazone, which was recently withdrawn from the U.S. market due to these concerns about toxicity. Because of the problems that have occurred with the glitazones, researchers in a number of laboratories have been investigating classes of PPAR agonists that are not glitazones and do not contain 1,3-thiazolidinedione moieties.

Compounds that are not glitazones but are agonists of PPAR sub-types are expected to be useful in the treatment of diabetes and associated conditions. PPARα agonists should improve the lipid profile and alleviate dyslipidemias by reducing elevated LDL levels and elevated triglyceride levels and/or increasing HDL levels. PPARγ agonists should improve insulin sensitivity, reducing the need for insulin injections in patients with NTDDM. The role of PPARδ is less well defined.

The class of compounds described herein is novel. Structurally similar kinds of compounds have been synthesized and invesigated for other uses, particularly leukotriene B4 antagonism. See for example, _____.

SUMMARY OF TEE INVENTION

The class of compounds described herein is a new class of PPAR agonists that do not contain a 1,3-thiazolidinedione moiety and therefore are not glitazones. The class of compounds includes compounds that are primarily PPARα agonists, compounds that are primarily PPARγ agonists, and compounds that are mixed PPARα/γ agonists. The clinical effects are expected to vary depending on the balance in agonism of the PPAR-subtypes. These compounds are useful in the treatment, control and/or prevention of diabetes, hyperglycemia, mixed or diabetic dyslipidemia, and other lipid disorders (including isolated hypercholesterolemia as manifested by elevations in LDL-C and/or non-HDL-C and/or hyperapoBliproteinemia, hypertriglyceridemia and/or increase in triglyceride-rich-lipoproteins, and low HDL cholesterol concentrations), atherosclerosis, obesity, vascular restenosis, inflammatory conditions, neoplastic conditions, and other PPARα and/or γ mediated diseases, disorders and conditions.

The present invention provides compounds having the structure of Formula I, including pharmaceutically acceptable salts and prodrugs of these compounds:

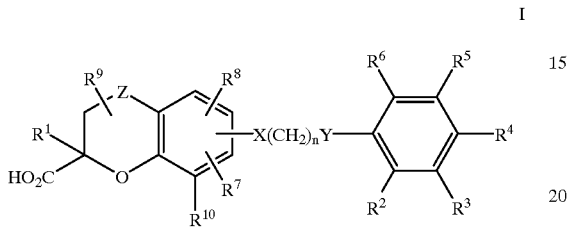

I

In the compounds of Formula I:

Z is selected from the group consisting of $CH_2$ and C=O;

$R^1$ is selected from H, —OH, $C_{1-7}$alkyl, $C_{2-7}$alkenyl, $C_{2-7}$alkynyl, —$OC_{1-3}$alkyl, —$OC_{2-3}$alkenyl, —$OC_{2-3}$alkynyl, F, Br, Cl, and Ar, wherein alkyl, alkenyl, alkynyl, —Oalkyl, —Oalkenyl and —Oalkynyl are linear or branched and are optionally substituted with (a) 1–7 halogen atoms and/or (b) 1–3 groups independently selected from (i) —$OC_{1-3}$alkyl, which is optionally substituted with 1–5 halogen atoms, and (ii) phenyl, which is optionally substituted with 1–3 groups independently selected from halogen, $C_{1-5}$alkyl and —$OC_{1-3}$alkyl, said $C_{1-5}$alkyl and —$OC_{1-3}$alkyl being linear or branched and optionally substituted with 1–5 halogens; or alternatively, $R^1$ is a group —$CR^{11}R^{12}$— which bridges between the carbon to which $R^1$ is attached in FIG. I and the adjacent carbon on the heterocyclic ring, yielding a cyclopropane ring;

$R^{11}$ and $R^{12}$ are independently selected from the group consisting of hydrogen, halogen, $C_{1-5}$alkyl, $C_{2-5}$alkenyl, $C_{2-5}$alkynyl, —$OC_{1-3}$alkyl, —$OC_{2-3}$alkenyl, —$OC_{2-3}$alkynyl, —$CO_2H$, —$CO_2C_{1-5}$alkyl, —$CO_2C_{2-5}$alkenyl, —$CO_2C_{2-5}$alkynyl, and phenyl, where alkyl, alkenyl, alkynyl, —Oalkyl, —Oalkenyl, —Oalkynyl —$CO_2$alkyl, —$CO_2$alkenyl, and —$CO_2$alkynyl are linear or branched and are optionally substituted with (a) 1–5 halogens and/or (b) 1–3 substituents independently selected from —$OCH_3$ and —$OCF_3$, and where phenyl is optionally substituted with 1–3 groups independently selected from halogen, $C_{1-5}$alkyl, and —$OC_{1-3}$alkyl, wherein $C_{1-5}$alkyl and —$OC_{1-3}$alkyl are linear or branched and are optionally substituted with 1–5 halogens;

Ar is selected from the group consisting of Aryl, Hetcyc, Hetaryl, and Benzoheterocycle, where Aryl, Hetcyc, Hetaryl, and Benzoheterocycle are in each instance optionally substituted with 1–5 substituents independently selected from (a) halogen, (b) $C_{1-5}$alkyl, (c) $C_{2-5}$alkenyl, (d) $C_{2-5}$alkynyl, (e) —$OC_{1-5}$alkyl, (f) —$OC_{2-5}$alkenyl, (g) —$OC_{2-5}$alkynyl, (h) —$SO_xC_{1-5}$alkyl, (i) —$SO_xNR^aR^b$, (j) —$SO_x$phenyl, (k) —C(O)$C_{1-3}$alkyl, and (l) —C(O)$NR^aR^b$, wherein in each instance, each alkyl, alkenyl and alkynyl is linear or branched and is optionally substituted with (a) 1–5 halogen atoms and/or (b) 1–2 groups independently selected from —$OC_{1-3}$alkyl, which is linear or branched and is optionally substituted with 1–5 halogens, and where phenyl is optionally substituted with 1–3 substituents independently selected from halogen, $C_{1-3}$alkyl, and $C_{1-3}$alkoxy, wherein $C_{1-3}$alkyl and $C_{1-3}$alkoxy are linear or branched and are optionally substituted with 1–5 halogens, and wherein Hetcyc and Benzoheterocycle may each optionally have a $C_{3-6}$-spiro-cycloalkyl substituent on the ring on a carbon atom that can have gem-disubstitution, wherein the spiro-cycloalkyl group is optionally substituted with 1–2 groups independently selected from methyl, trifluoromethyl, methoxy, trifluoromethoxy and halogen;

x is selected from 0, 1 and 2;

Aryl is a carbocyclic 6–10 membered monocyclic or bicyclic aromatic ring system;

Hetcyc is a 5- or 6-membered saturated or partly saturated monocyclic heterocycle having 1–4 heteroatoms independently selected from N, S and O in the perimeter of the ring, wherein N may optionally be $NR^a$ and S may optionally be SO or $SO_2$;

Hetaryl is a 5- or 6-membered heteroaromatic ring having 1–4 heteroatoms independently selected from O, S, and N in the perimeter of the ring, where N may optionally be $NR^a$, and S may optionally be SO or $SO_2$;

Benzoheterocycle comprises a 5 or 6-membered heterocyclic ring which may be saturated, partly unsaturated or aromatic, and a benzene ring, wherein said heterocyclic ring and said benzene ring are fused together, wherein said heterocyclic ring comprises 1–3 heteroatoms independently selected from O, S, and N in the perimeter of the ring, where N may optionally be $NR^a$, and S may optionally be SO or $SO_2$;

$R^a$ and $R^b$ are independently selected from the group consisting of H, $C_{1-5}$alkyl, $C_{2-5}$alkenyl, $C_{2-5}$alkynyl, —C(O)$C_{1-5}$alkyl, —C(O)$C_{2-5}$alkenyl, —C(O)$C_{2-5}$alkynyl, $SO_xC_{1-5}$alkyl, $SO_x$phenyl, $SOxNR^dR^e$, —C(O)$NR^dR^e$, halogen, and phenyl, wherein in all instances, alkyl, alkenyl, and alkynyl are linear or branched and are optionally substituted with (a) 1–5 halogen atoms and/or (b) 1–3 groups independently selected from —$OCH_3$, —$OCF_3$ and phenyl, wherein phenyl in all occurrences is optionally substituted with 1–3 substituents independently selected from halogen, $C_{1-3}$alkyl, and $C_{1-3}$alkoxy, said $C_{1-3}$alkyl and $C_{1-3}$alkoxy being linear or branched and optionally substituted with 1–5 halogens;

$R^d$ and $R^e$ are independently selected from H, $C_{1-5}$alkyl, $C_{2-5}$alkenyl, $C_{2-5}$alkynyl, and phenyl, wherein said alkyl, alkenyl, and alkynyl are linear or branched and are optionally substituted with (a) 1–5 halogen atoms and/or (b) 1–3 groups independently selected from —$OCH_3$, —$OCF_3$ and phenyl, wherein phenyl in all occurrences is optionally substituted with 1–3 substituents independently selected from halogen, $C_{1-3}$alkyl, and $C_{1-3}$alkoxy, said $C_{1-3}$alkyl and $C_{1-3}$alkoxy being linear or branched and optionally substituted with 1–5 halogens;

X and Y are independently selected from the group consisting of O, S, SO, $SO_2$, $NR^a$ and $CH_2$;

n is an integer from 1–6;

$R^2$, $R^3$, $R^5$, $R^6$, $R^7$, $R^8$, $R^9$ and $R^{10}$ are independently selected from H, halogen, $C_{1-7}$alkyl, $C_{2-7}$alkenyl, $C_{2-7}$alkynyl, —OH, —$OC_{1-5}$alkyl, —$OC_{2-5}$alkenyl, —$OC_{2-5}$alkynyl, —$C(O)C_{1-5}$alkyl, —$C(O)C_{2-5}$alkenyl, —$C(O)C_{2-5}$alkynyl, —$C(O)OC_{1-5}$alkyl, —$C(O)OC_{2-5}$alkenyl, —$C(O)OC_{2-5}$alkynyl, —$OC(O)C_{1-5}$alkyl, —$OC(O)C_{2-5}$alkenyl, —$OC(O)C_{2-5}$alkynyl, Ar, —OAr, —C(O)Ar, —C(O)OAr, —OC(O)Ar, $C_{3-8}$Cycloalkyl, —$OC_{3-8}$Cycloalkyl, —$SO_xC_{1-5}$alkyl, —$SO_xNR^aR^b$, —$SO_xAr$, and —$C(O)NR^aR^b$, wherein in each instance, each alkyl, alkenyl, and alkynyl is linear or branched and is optionally substituted with (a) 1–5 halogen atoms and/or (b) 1–2 groups independently selected from —$OC_{1-3}$alkyl groups which are linear or branched and are optionally substituted with 1–5 halogens and/or (c) 1 group Ar or $C_{3-6}$Cycloalkyl; and $R^4$ is OAr.

In the description above and elsewhere, including the claims, when something is described as being "optional," such as 1 or more substituents or compounds from a list of substituents or compounds, one of the options is that the substituent or compound may be absent.

These compounds are effective in lowering glucose, lipids, and insulin in diabetic animals. The compounds are expected to be efficacious in the treatment, control and/or prevention of non-insulin dependent diabetes mellitus (NIDDM) in humans and in the treatment, control, and/or prevention of conditions associated with NIDDM, including hyperlipidemia, dyslipidemia, obesity, hypercholesterolemia, hypertrigyceridemia, atherosclerosis, vascular restenosis, inflammatory conditions, neoplastic conditions, and other PPARα and/or γ mediated diseases, disorders and conditions.

DETAILED DESCRIPTION OF THE INVENTION

The invention has numerous embodiments. Several groups of compounds are described below:

One group of compounds of formula I includes compounds in which X and Y are each O or S. Another group of compounds includes those in which X and Y are O.

One embodiment includes all compounds where Z is $CH_2$. Another embodiment includes those compounds in which Z is C=O.

Another embodiment includes those compounds in which n is 3 or 4.

A preferred group of compounds includes those compounds in which $R^1$ is selected from Cl, Br, F and $C_{1-4}$ alkyl, where $C_{1-4}$alkyl is linear or branched and is optionally substituted with (a) 1–3 halogens independently selected from F and Cl, (b) 1 phenyl which is optionally substituted with 1–3 halogens, or (c) a mixture thereof.

Another preferred group of compounds of formula I includes those compounds in which $R^2$ is selected from the group consisting of Cl, Br, F and $C_{1-4}$alkyl, where $C_{1-4}$alkyl is linear or branched and is optionally substituted with 1–3 halogens.

In another group of compounds having formula I, group —X— is attached to the benzopyran ring at the 6-position of the benzopyran ring. In a different group of compounds having formula I, the group —X— is attached to the benzopyran ring at the 7-position of the benzopyran ring.

In other groups of compounds having formula I, $R^1$ is selected from $C_{1-4}$alkyl, Cl and F, where alkyl is linear or branched and is optionally substituted with 1–5 F.

A preferred group of compounds of formula I comprises compounds in which Ar is phenyl, which is optionally substituted with 1–4 groups independently selected from Cl, F, $C_{1-5}$alkyl, —$OCH_3$, —$OCF_3$, —$SO_xC_{1-5}$alkyl, —$SO_xNR_aR_b$, —$SO_x$phenyl, —$C(O)C_{1-3}$alkyl, and —$C(O)NR^aR^b$, where phenyl of —$SO_x$phenyl is optionally substituted with 1–3 substituents independently selected from halogen, $CH_3$, $CF_3$, —$OCF_3$, and —$OCH_3$, and where alkyl in all occurrences is linear or branched and is optionally substituted with 1–5 halogens.

In another preferred subset of compounds having Formula I, $R^1$ and $R^2$ are each selected from $C_{1-4}$alkyl, Cl and F; n is 2–4; X and Y are O; Z is $CH_2$; and $R^3$, $R^5$, $R^6$, $R^7$, $R^8$, $R^9$ and $R^{10}$ are each selected from H, Cl, F, $CH_3$, and $CF_3$. Any alkyl in this group of compounds is linear or branched and is optionally substituted with 1–5 F. In a selected group of compounds, Z is $CH_2$. In most compounds, $R^3$, $R^5$, $R^6$, $R^7$, $R^8$, $R^9$ and $R^{10}$ are preferably H.

Another embodiment includes compounds having formula I as previously described, where $R^3$, $R^5$, $R^6$, $R^7$, $R^8$, $R^9$, and $R^{10}$ are H; $R^2$ is Cl or F; and $R^1$ is $C_{1-4}$alkyl, Cl or F, where $C_{1-4}$alkyl is linear or branched and is optionally substituted with 1–5 F.

In another embodiment, $R^3$, $R^5$ and $R^6$ are all H.

Another subset comprises compounds in which $R^a$ and $R^b$ are independently selected from H, $C_{1-5}$alkyl, —$C(O)C_{1-5}$alkyl, —$S(O)_xC_{1-5}$alkyl, —$S(O)_x$phenyl, and phenyl. In these compounds, each alkyl group is linear or branched and is optionally substituted with 1–5 halogen atoms. Each phenyl is optionally substituted with 1–3 substituents independently selected from halogen, $C_{1-3}$alkyl, and $C_{1-3}$alkoxy, and these $C_{1-3}$alkyl and $C_{1-3}$alkoxy substituents are linear or branched and are optionally substituted with 1–5 halogens.

Another group of compounds is defined as those compounds having Formula I in which $R^1$ is neither H or —$CR^{11}R^{12}$—, and no more than one of $R^2$, $R^6$, and $R^{10}$ is alkyl.

In other preferred compounds having Formula I, $R^2$ is Cl, Br or F, and $R^{10}$ is not an alkyl group of any length.

Specific examples of compounds of this invention are provided as Examples 1–29, listed by name below. Their structures are illustrated in the Table immediately before the Examples.

The following compounds, including pharmaceutically acceptable salts and prodrugs of these compounds, are specific embodiments of this invention:

Example 1: 7-(3-(2-Propyl-4-phenoxyphenoxy)propoxy)-chromane-2-carboxylic acid;

Example 2: 7-(3-(2-Propyl-4-phenoxphenoxy)propoxy)-2-propylchromane-2-carboxylic acid;

Example 3: 7-(4-(2-Propyl-4-phenoxyphenoxy)butoxy)-chromane-2-carboxylic acid;

Example 4: 7-(4-(2-Propyl-4-phenoxyphenoxy)butoxy)-2-methylchromane-2-carboxylic acid;

Example 5: 7-(3-(2-Propyl-4-(4-chlorophenoxy)phenoxy) propoxy)-2-ethylchromane-2-carboxylic acid;

Example 6: 7-(3-(2-Propyl-4-(4-fluorophenoxy)phenoxy) propoxy)-2-ethylchromane-2-carboxylic acid;

Example 7: 7-(3-(2-Propyl-4-(4-methoxyphenoxy) phenoxy)propoxy)-2-ethylchromane-2-carboxylic acid;

Example 8: 7-(3-(4-Phenoxyphenoxy)propoxy)-2-ethylchromane-2-carboxylic acid;

Example 9: 7-(3-(2-Propyl-4-(4-methylsulfonylphenoxy) phenoxy)propoxy)-2-ethylchromane-2-carboxylic acid;

Example 10: 7-(3-(2-Propyl-4-(4-isobutylphenoxy) phenoxy)propoxy)-2-ethylchromane-2-carboxylic acid;

Example 11: 7-(2-(2-Propyl-4-phenoxyphenoxy)ethoxy)-2-ethylchromane-2-carboxylic acid;

Example 12: 7-(2-(2-Propyl-4-(4-methylsulfonylphenoxy)phenoxy)ethoxy)-2-ethylchromane-2-carboxylic acid;

Example 13: 6-(3-(2-Propyl-4-phenoxyphenoxy) propoxy)-chromane-2-carboxylic acid;

Example 14: 6-(3-(2-Propyl-4-phenoxyphenoxy) propoxy)-2-methylchromane-2-carboxylic acid;

Example 15: 6-(4-(2-Propyl-4-phenoxyphenoxy)butoxy)-chromane-2-carboxylic acid;

Example 16: 6-(4-(2-Propyl-4-phenoxyphenoxy)butoxy)-2-methyl-chromane-2-carboxylic acid;

Example 17: 7-(3-(2-Chloro-4-phenoxyphenoxy) propoxy)-chromane-2-carboxylic acid;

Example 18: 7-(3-(2-Chloro-4-phenoxyphenoxy) propoxy)-2-methylchromane-2-carboxylic acid;

Example 19: 7-(3-(2-Chloro-4-phenoxyphenoxy) propoxy)-2-ethylchromane-2-carboxylic acid;

Example 20: 7-(3-(2-Chloro-4-(4-fluorophenoxy) phenoxy)propoxy)-chromane-2-carboxylic acid;

Example 21: 7-(3-(2-Chloro-4-(4-fluorophenoxy) phenoxy)propoxy)-2-ethylchromane-2-carboxylic acid;

Example 22: 7-(3-(2-Chloro-4-(4-fluorophenoxy) phenoxy)propoxy)-2-propylchromane-2-carboxylic acid;

Example 23: 7-(3-(2-Fluoro-4-phenoxyphenoxy) propoxy)-2-ethylchromane-2-carboxylic acid;

Example 24: 7-(3-(2-Chloro-4-(4-fluorophenoxy) phenoxy)propoxy)-2-(4-fluorophenylmethyl)-chromane-2-carboxylic acid;

Example 25: (2R)-7-(3-(2-Chloro-4-phenoxyphenoxy) propoxy)-2-ethylchromane-2-carboxylic acid;

Example 26: (2R)-7-(3-(2-Chloro-4-(4-fluorophenoxy) phenoxy)propoxy)-2-ethylchromane-2-carboxylic acid;

Example 27: (2S)-7-(3-(2-Chloro-4-phenoxyphenoxy) propoxy)-2-ethylchromane-2-carboxylic acid;

Example 28: (2S)-7-(3-(2-Chloro-4-(4-fluorophenoxy) phenoxy)propoxy)-2-ethylchromane-2-carboxylic acid;

Example 29: (2R)-7-(3-(2-Propyl-4-(4-isobutylphenoxy) phenoxy)propoxy)-2-propylchromane-2-carboxylic acid.

The invention further includes pharmaceutical compositions comprising any of the compounds described above and a pharmaceutically acceptable carrier.

The compounds as defined above are useful in treating, controlling, and preventing the following diseases, and may also be used in treating other diseases not listed below:

(1) a method for treating, controlling or preventing diabetes mellitus, and particularly non-insulin dependent diabetes mellitus, in a mammalian patient in need of such treatment which comprises administering to the patient a therapeutically effective amount of a compound of Formula I;

(2) a method for treating, controlling, or preventing hyperglycemia in a mammalian patient in need of such treatment which comprises administering to the patient a therapeutically effective amount of a compound of Formula I;

(3) a method for treating, controlling, or preventing lipid disorders, hyperlipidemia, or low HDL in a mammalian patient in need of such treatment which comprises administering to the patient a therapeutically effective amount of a compound of Formula I;

(4) a method for treating, controlling, or preventing obesity in a mammalian patient in need of such treatment which comprises administering to the patient a therapeutically effective amount of a compound of Formula I;

(5) a method for treating, controlling, or preventing hypercholesterolemia in a mammalian patient in need of such treatment which comprises administering to the patient a therapeutically effective amount of a compound of Formula I;

(6) a method for treating, controlling, or preventing hypertriglyceridemia in a mammalian patient in need of such treatment which comprises administering to the patient a therapeutically effective amount of a compound of Formula I;

(7) a method for treating, controlling, or preventing dyslipidemia, including low HDL cholesterol, in a mammalian patient in need of such treatment which comprises administering to the patient a therapeutically effective amount of a compound of Formula I;

(8) a method for treating, controlling, or preventing atherosclerosis in a mammalian patient in need of such treatment which comprises administering to the patient a therapeutically effective amount of a compound of Formula I; it is understood that the sequellae of atherosclerosis (angina, claudication, heart attack, stroke, etc.) are thereby treated; and (9) a method for treating, controlling, or preventing cachexia in a mammalian patient in need of such treatment which comprises administering to the patient a therapeutically effective amount of a compound of Formula I.

Definitions

"Ac" is acetyl, which is $CH_3C(O)$—.

"Alkyl", as well as other groups having the prefix "alk", such as alkoxy or alkanoyl, means carbon chains which may be linear or branched or combinations thereof, unless the carbon chain is defined otherwise. Examples of alkyl groups include methyl, ethyl, propyl, isopropyl, butyl, sec- and tert-butyl, pentyl, neopentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means saturated or partly saturated monocyclic or bicyclic carbocyclic rings, each having from 3 to 10 carbon atoms, unless otherwise defined. The term also can include a monocyclic ring fused to an aryl group or other ring system. Examples of cycloalkyl include cyclopropyl, cyclobutyl, cyclopentyl, cyclohexyl, cycloheptyl, and the like.

"Aryl" (and "arylene") means mono- or bicyclic aromatic rings containing only carbon ring atoms. Aryl groups that are substituents herein are 6–10-membered monocyclic or bicyclic ring systems, and are preferably phenyl or naphthyl. Phenyl is most preferred. The term also may describe an aryl group fused to a monocyclic cycloalkyl or monocyclic heterocyclic group. "Heterocyclyl," "Heterocycle," and "heterocyclic" means a fully or partially saturated monocyclic or polycyclic ring system containing at least one heteroatom selected from N, S and O, each of said rings having from 3 to 10 atoms, except where defined otherwise. Examples of aryl include phenyl and naphthyl, as well as the phenyl ring of indanyl, indenyl, and tetrahydronaphthyl. Examples of aryl fused to heterocyclic groups include 2,3-dihydrobenzofuranyl, dihydrobenzopyranyl, and the like. Examples of heterocycles include tetrahydrofuran, piperazine, tetrahydropyran, and morpholine.

"Hetaryl" (and heteroarylene) means a mono-, bi- or tricyclic aromatic ring containing 1–4 ring heteroatoms selected from N, O and S (including SO and $SO_2$) in the perimeter of the ring, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzothiophenyl (including S-oxide and dioxide), furo(2,3-b)pyridyl, quinolyl, indolyl, isoquinolyl, dibenzofuran and the like.

"Halogen" includes fluorine, chlorine, bromine and iodine. Preferred halogens are chlorine and fluorine.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Optical Isomers—Diastereomers—Geometric Isomers—Tautomers

Compounds of Formula I contain at least one asymmetric center and may contain more than one asymmetric center. The compounds can thus occur as racemic mixtures, single enantiomers, diastereomeric mixtures and individual diastereomers. The present invention is meant to comprehend all such isomeric forms of the compounds of Formula I.

The compounds of Formula I all have an asymmetric center at the 2-position of the benzopyran ring, at the position where the carboxyl group is attached to the ring. One or both enantiomers of some of the compounds described below have been isolated. The R enantiomer has higher activity than the S enantiomer in experiments performed to date, and is therefore the preferred enantiomer. Although the S enantiomer has less activity than the R enantiomer, the S enantiomer has different selectivity, and for some of the compounds has sufficient activity that it may also be useful in the treatment of PPAR mediated diseases. For example, many of the R-enantiomers have both PPARα and PPARγ activity (i.e., they are PPARα/γ dual agonists), whereas the S enantiomers of the same compounds are often more γ-selective.

Some of the compounds described herein contain olefinic double bonds, and unless specified otherwise, are meant to include both E and Z geometric isomers.

Some of the compounds described herein may exist with different points of attachment of hydrogen coupled with double bond shifts, referred to as tautomers. Such an example may be a carbonyl (e.g. a ketone) and its enol form, often known as keto-enol tautomers. The individual tautomers as well as mixtures thereof are encompassed with compounds of Formula I.

If desired, racemic mixtures of compounds of Formula I may be separated by means of classical resolution through fractional crystallization of salts formed with enantiomerically pure acids or bases. Other diasteromeric derivatives can be formed by the coupling of a racemic mixture of the compounds of Formula I to an enantiomerically pure compound. Such diastereomeric mixture may be separated by standard chromatographic methods or recrystallization protocols. These diasteromeric derivatives may then be converted to the pure enantiomers of the compounds of Formula I by cleavage of the added chiral residue. The racemic mixture of the compounds of Formula I can also be separated directly by chromatographic methods utilizing chiral stationary phases, of which many examples are known in the literature.

Alternatively, any enantiomer of a compound of the general Formula I may be obtained by stereoselective synthesis using optically pure starting materials or reagents of known configuration.

Compounds of Formula I that have more than one asymmetric center and that occur as diasteromeric mixtures can similarly be separated into individual diastereomers by standard methods, and these can be separated to individual enantiomers as described above.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites—Prodrugs

This invention also includes the active metabolites of claimed compounds. Prodrugs, which are compounds that are converted to the claimed compounds as they are being administered to a patient or after they have been administered to a patient, are also included within the scope of the claimed active compounds. A non-limiting example of a prodrug of the carboxylic acids of this invention would be an ester of the carboxylic acid group, for example a $C_1$ to $C_6$ ester, which may be linear or branched, or an ester which has functionality that makes it more easily hydrolyzed after administration to a patient.

Examples of prodrugs of this class of compounds may be described as compounds having the Formula Ia:

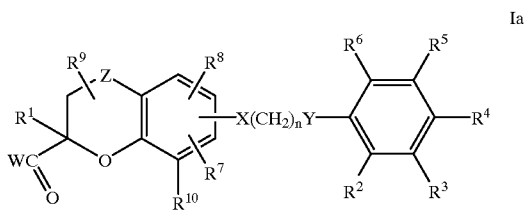

$R^1, R^2, R^3, R^4, R^5, R^6, R^7, R^8, R^9, R^{10}, R^{11}, R^{12}, R^a, R^b, R^d, R^e$, X, Y, Z, n, x, Ar, and other substituents are as defined previously. In the prodrugs, W is a group that is easily removed under physiological conditions during or after administration to a mammalian patient to yield a compound having Formula I, or the carboxylate anion thereof (in solution), or a pharmaceutically acceptable salt thereof.

Examples of prodrugs of Formula Ia include compounds in which W is selected from the group consisting of —$OR^{13}$, $OCH_2OR^{13}$, —$OCH(CH_3)OR^{13}$, —$OCH_2OC(O)R^{13}$, —$OCH(CH_3)OC(O)R^{13}$, —$OCH_2OC(O)OR^{13}$, —OCH$(CH_3)OC(O)OR^{13}$, and —$NR^{14}R^{14}$, where each $R^{13}$ is independently selected from $C_{1-6}$ alkyl optionally substituted with one or two groups selected from —$CO_2H$, —$CONH_2$, —$NH_2$, —OH, —OAc, —NHAc, and phenyl; and wherein each $R^{14}$ is independently selected from H and R13. Compounds having Formula Ia, where W has the chemical structure described above, are described as prodrugs. However, regardless of whether they are active as prodrugs, yielding compounds or salts of Formula I, or whether they have a different means of exhibiting pharmaceutical activity, the compounds of Formula Ia are included in this invention. Such compounds are claimed herein, regardless of the mechanism leading to their activity.

The description of utility, pharmaceutical compositions, combination therapies, administration, dosage, and the like that are described herein are applicable to the prodrugs described above and to the compounds described previously.

Utilities

Compounds of the present invention are potent agonists of various peroxisome proliferator activator receptor subtypes, particularly PPARα and/or PPARγ. Compounds of the present invention may be selective agonists of one receptor subtype, e.g. PPARγ or PPARα agonists, or they may be agonists of more than one receptor subtypes, e.g. dual PPARα/γ agonists. Compounds of the present invention are useful in treating, controlling or preventing diseases, disorders or conditions, wherein the treatment is mediated by the activation of an individual PPAR subtype (α or γ), or a combination of PPAR subtypes (e.g. α/γ). Thus one aspect of the present invention provides a method for the treatment, control or prevention of such diseases, disorders, or conditions in a mammal which comprises administering to such mammal a therapeutically effective amount of a compound of Formula I. The diseases, disorders or conditions for which compounds of the present invention are useful in treating, controlling or preventing include, but are not limited to, (1) diabetes mellitus, and especially non-insulin dependent diabetes mellitus (NIDDM), (2) hyperglycemia, (3) impaired glucose tolerance, (4) insulin resistance, (5) obesity, (6) lipid disorders, (7) dyslipidemia, (8) hyperlipidemia, (9) hypertriglyceridemia, (10)hypercholesterolemia, (11) low HDL levels, (12) high LDL levels, (13) atherosclerosis and its sequelae, (14) vascular restenosis, (15) irritable bowel syndrome, (16) inflammatory bowel disease, including Crohn's disease and ulcerative colitis, (17) other inflammatory conditions, (18) pancreatitis, (19) abdominal obesity, (20) neurodegenerative disease, (21) retinopathy, (22) neoplastic conditions, (23) adipose cell tumors, (24) adipose cell carcinomas, such as liposarcoma, (25) prostate cancer and other cancers, including gastric, breast, bladder and colon cancers, (26) angiogenesis, (27) Alzheimer's disease, (28) psoriasis, (29) acne vulgaris, (30) other skin diseases and dermatological conditions modulated by PPAR, (31) high blood pressure, (32) Syndrome X, (33) ovarian hyperandrogenism (polycystic ovarian syndrome), and other disorders where insulin resistance is a component.

Another aspect of the invention provides a method for the treatment, control, or prevention of hypercholesterolemia, atherosclerosis, low HDL levels, high LDL levels, hyperlipidemia, hypertriglyceridemia, and/or dyslipidemia, which comprises administering to a mammal in need of such treatment a therapeutically effective amount of an agonist of PPARα and/or PPARγ or a PPARα/γ dual agonist. The PPAR agonist may be used alone or advantageously may be administered with a cholesterol biosynthesis inhibitor, including but not limited to, an HMG-CoA reductase inhibitor such as lovastatin, simvastatin, pravastatin, fluvastatin, atorvastatin, rivastatin, itavastatin, or ZD-4522. The PPAR agonist may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), and with niacin, bile acid sequestrants, microsomal triglyceride transport inhibitors, and bile acid reuptake inhibitors. These combination treatments may also be effective for the treatment, control or prevention of one or more related conditions selected from the group consisting of hypercholesterolemia, atherosclerosis, hyperlipidemia, hypertriglyceridemia, dyslipidemia, high LDL, and low HDL.

Another aspect of the invention provides a method of treating inflammatory conditions, including inflammatory bowel disease, Crohn's disease, and ulcerative colitis by administering an effective amount of a PPAR agonist, which may be a PPARα agonist, a PPARγ agonist, or a PPARα/γ dual agonist. Additional inflammatory diseases that may be treated with the instant invention include gout, rheumatoid arthritis, osteoarthritis, multiple sclerosis, asthma, ARDS, psoriasis, vasculitis, ischemia/reperfusion injury, frostbite, and related diseases.

Another aspect of the invention provides a method of treating cachexia. PPARα is known to be necessary for an appropriate energy sparing response to starvation, and inappropriate metabolism and energy utilization is clearly responsible for the wasting of cachexia.

Another aspect of the invention provides a method of treating a variety of skin diseases and dermatological conditions that are modulated by PPARα and/or γ agonists. These diseases and conditions include psoriasis and acne vulgaris. Examples of other skin diseases and dermatological disorders that may be treated include eczema; lupus associated skin lesions; dermatitides such as seborrheic dermatitis and solar dermatitis; keratoses such as seborrheic keratosis, senile keratosis, actinic keratosis, photo-induced keratosis, and keratosis follicularis; keloids and prophylaxis against keloid formation, warts including verruca, condyloma, or condyloma accuminatum, and human papilloma viral (HPV) infections such as venereal warts, viral warts, molluscum contagiosum, leukoplakia, lichen planus; keratitis, skin cancer such as basal cell carcinoma, cutaneous T cell lymphoma and localized benign epidermal tumors (keratoderma, epidermal naevi).

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing diabetes mellitus and/or hyperglycemia or hypertriglyceridemia or other diseases for which compounds of Formula I are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt or prodrug thereof as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of Formula I may be used in combination with other drugs that may also be useful in the treatment, prevention, suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) insulin sensitizers including (i) PPARγ agonists such as the glitazones (e.g. troglitazone, pioglitazone, englitazone, MCC-555, rosiglitazone, and the like), and compounds disclosed in WO97/27857, 97/28115, 97/28137 and 97/27847; (ii) biguanides such as metformin and phenformin; (iii) protein tyrosine phosphatase-1B (PTP-1B) inhibitors, and (iv) dipeptidyl peptidase IV (DP-IV) inhibitors;

(b) insulin or insulin mimetics;

(c) sulfonylureas such as tolbutamide and glipizide, or related materials;

(d) α-glucosidase inhibitors (such as acarbose);

(e) cholesterol lowering agents such as (i) EDNG-CoA reductase inhibitors (lovastatin, simvastatin, pravastatin, fluvastatin, atorvastatin, rivastatin, itavastatin, 2D-4522 and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fibric acid derivatives (clofibrate, fenofibrate and bezafibrate) or gemfibrozil (v) PPARα/γ dual agonists, such as KRP-297, (vi) inhibitors of cholesterol absorption, such as for example ezetimibe, (vii) acyl CoA:cholesterol acyltransferase inhibitors, such as for example avasimnibe, and (viii) anti-oxidants, such as probucol;

(f) PPARδ agonists such as those disclosed in WO97/28149;

(g) antiobesity compounds (anorectics) such as fenfluramine, dexfenfluramine, phentermine, sibutramine, mazindol, orlistat, lipase inhibitors, neuropeptide Y5 inhibitors, and $β_3$ adrenergic receptor agonists;

(h) an ileal bile acid transporter inhibitor; and (i) agents intended for use in inflammatory conditions such as aspirin, non-steroidal anti-inflammatory drugs, glucocorticoids, azulfidine, and cyclo-oxygenase 2 selective inhibitors.

The above combinations include combinations of a compound of the present invention not only with one other active compound, but also with two or more other active compounds. Non-limiting examples include combinations of compounds having Formula I with two or more active compounds selected from biguanides, sulfonylureas, HMG-CoA reductase inhibitors, other PPAR agonists, PTP-1B inhibitors, DP-IV inhibitors, and anti-obesity compounds.

BIOLOGICAL ASSAYS

A) PPAR Binding Assays

For preparation of recombinant human PPARγ, PPARδ, and PPARα: Human PPARγ$_2$, human PPARδ and human PPARα were expressed as gst-fusion proteins in *E. coli*. The full length human cDNA for PPARγ$_2$ was subcloned into the pGEX-2T expression vector (Pharmacia). The full length human cDNAs for PPARδ and PPARα were subcloned into the pGEX-KT expression vector (Pharmacia). *E. coli* containing the respective plasmids were propagated, induced, and harvested by centrifugation. The resuspended pellet was broken in a French press and debris was removed by centrifugation at 12,000×g. Recombinant human PPAR receptors were purified by affinity chromatography on glutathione sepharose. After application to the column, and one wash, receptor was eluted with glutathione. Glycerol (10%) was added to stabilize the receptor and aliquots were stored at −80° C.

For binding to PPARγ, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamidine and 0.5 mM PMSF) containing 0.1% non-fat dry milk and 10 nM [$^3$H$_2$] AD5075, (21 Ci/mmole), ±test compound as described in Berger et al (Novel peroxisome proliferator-activated receptor (PPARγ) and PPARδ ligands produce distinct biological effects. J. Biol. Chem. (1999), 274: 6718–6725.) Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

For binding to PPARδ, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamide and 0.5 mM PMSF) containing 0.1 % non-fat dry milk and 2.5 nM [$^3$H$_2$]L-783483, (17 Ci/mmole), ±test compound as described in Berger et al (Novel peroxisome proliferator-activated receptorγ (PPARγ) and PPARδ ligands produce distinct biological effects.1999 J Biol Chem 274: 6718–6725). (L-783483 is 3-chloro-4-(3-(7-propyl-3-trifluoromethyl-6-benz-[4,5]-isoxazoloxy) propylthio)phenylacetic acid, Ex. 20 in WO 97/28137). Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

For binding to PPARα, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 ag/mL leupeptin, 2 μg/mL benzamide and 0.5 mM PMSF) containing 0.1% non-fat dry milk and 5.0 nM [$^3$H$_2$](3-(4-(3-phenyl-7-propyl-6-benz-[4,5]-isoxazoloxy)butyloxy))phenylacetic acid (34 Ci/mmole), ±test compound. This is a tritium labelled variant of Ex.62 in WO 97/28137. Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

B). Gal-4 hPPAR Transactivation Assays

The chimeric receptor expression constructs, pcDNA3-hPPARγ/GAL4, pcDNA3-hPPARδ/GAL4, pcDNA3-hPPARα/GAL4 were prepared by inserting the yeast GAL4 transcription factor DBD adjacent to the ligand binding domains (LBDs) of hPPARγ, hPPARδ, hPPARα, respectively. The reporter construct, pUAS(5X)-tk-luc was generated by inserting 5 copies of the GAL4 response element upstream of the herpes virus minimal thymidine kinase promoter and the luciferase reporter gene. pCMV-lacZ contains the galactosidase Z gene under the regulation of the cytomegalovirus promoter. COS-1 cells were seeded at 12×10³ cells/well in 96 well cell culture plates in high glucose Dulbecco's modified Eagle medium (DMEM) containing 10% charcoal stripped fetal calf serum (Gemini Bio-Products, Calabasas, Calif.), nonessential amino acids, 100 units/ml Penicillin G and 100 mg/ml Streptomycin sulfate at 37 ° C. in a humidified atmosphere of 10% CO$_2$. After 24 h, transfections were performed with Lipofectamine (GIBCO BRL, Gaithersburg, Md.) according to the instructions of the manufacturer. Briefly, transfection mixes for each well contained 0.48 μl of Lipofectamine, 0.00075 μg of pcDNA3-PPAR/GALA expression vector, 0.045 μg of pUAS(5X)-tk-luc reporter vector and 0.0002 μg of pCMV-lacZ as an internal control for transactivation efficiency. Cells were incubated in the transfection mixture for 5 h at 37° C. in an atmosphere of 10% CO$_2$. The cells were then incubated for ~48 h in fresh high glucose DMEM containing 5% charcoal stripped fetal calf serum, nonessential amino acids, 100 units/mi Penicillin G and 100 mg/ml Streptomycin sulfate±increasing concentrations of test compound. Since the compounds were solubilized in DMSO, control cells were incubated with equivalent concentrations of DMSO; final DMSO concentrations were ≦0.1%, a concentration which was shown not to effect transactivation activity. Cell lysates were produced using Reporter Lysis Buffer (Promega, Madison, Wis.) according to the manufacturer's instructions. Luciferase activity in cell extracts was determined using Luciferase Assay Buffer (Promega, Madison, Wis.) in an ML3000 luminometer (Dynatech Laboratories, Chantilly, Va.). β-galactosidase activity was determined using β-D-galactopyranoside (Calbiochem, San Diego, Calif.).

C. In Vivo Studies

Male db/db mice (10–11 week old C57BI/KFJ, Jackson Labs, Bar Harbor, Me.) were housed 5/cage and allowed ad lib. access to ground Purina rodent chow and water. The animals, and their food, were weighed every 2 days and were dosed daily by gavage with vehicle (0.5% carboxymethylcellulose)±test compound at the indicated dose. Drug suspensions were prepared daily. Plasma glucose, and triglyceride concentrations were determined from blood obtained by tail bleeds at 3–5 day intervals during the study period. Glucose, and triglyceride, determinations were performed on a Boehringer Mannheim Hitachi 911 automatic analyzer (Boehringer Mannheim, Indianapolis, Ind.) using heparinized plasma diluted 1:6 (v/v) with normal saline. Lean animals were age-matched heterozygous mice maintained in the same manner.

TABLE OF COMPOUNDS
The table below illustrates compounds that were synthesized in accordance with the present invention. Detailed synthesis are provided in the Examples.

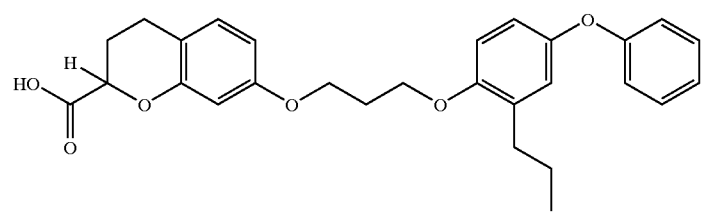

Example 1

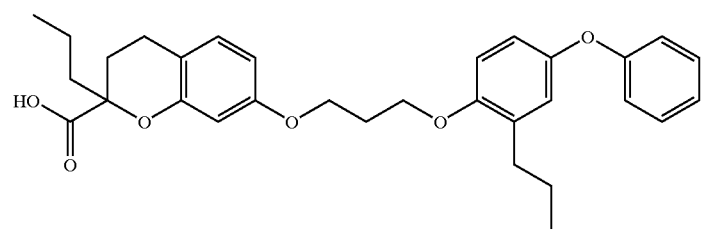

Example 2

TABLE OF COMPOUNDS
The table below illustrates compounds that were synthesized in accordance with the present invention. Detailed synthesis are provided in the Examples.
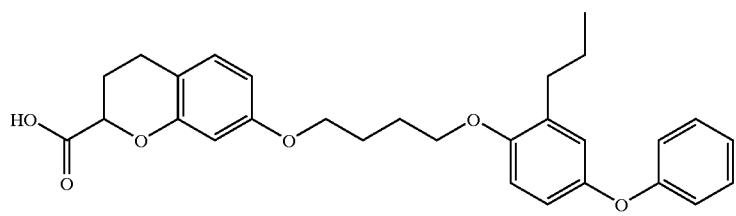
Example 3
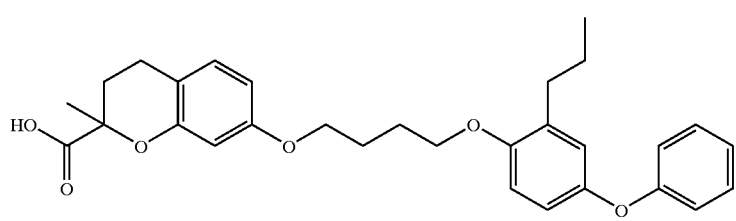
Example 4
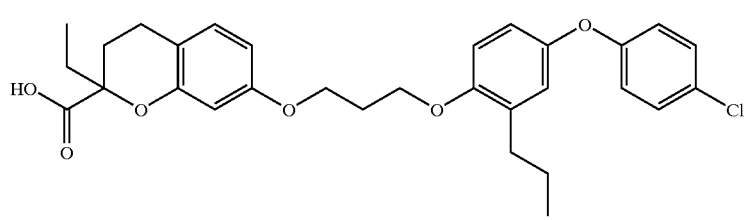
Example 5
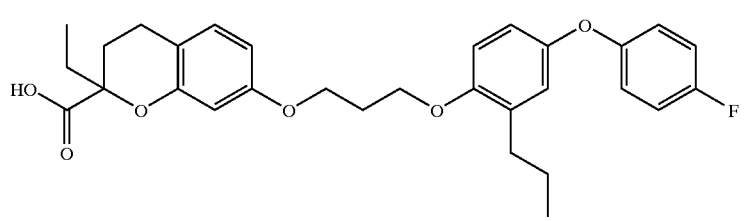
Example 6
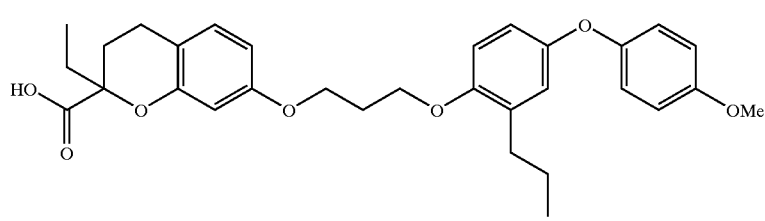
Example 7
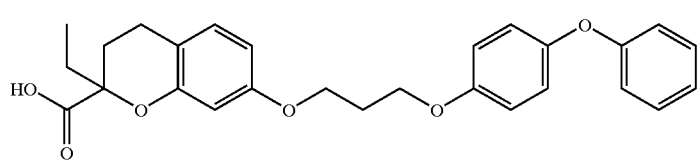
Example 8
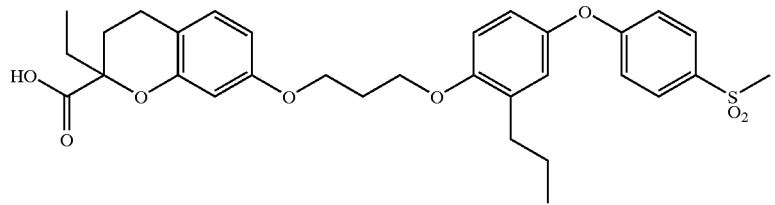
Example 9

-continued
TABLE OF COMPOUNDS
The table below illustrates compounds that were synthesized in accordance with the present invention. Detailed synthesis are provided in the Examples.
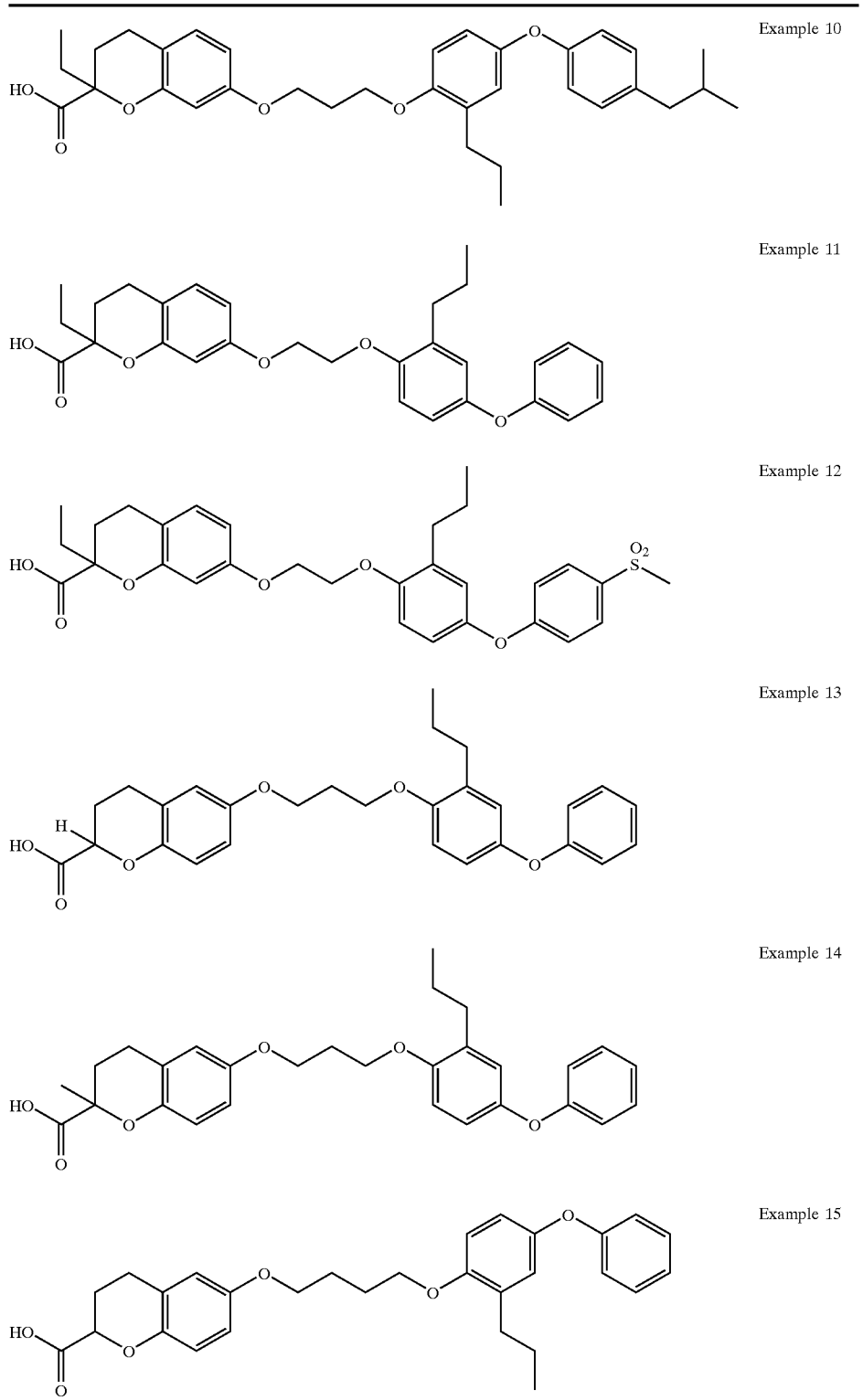
Example 10
Example 11
Example 12
Example 13
Example 14
Example 15

-continued
TABLE OF COMPOUNDS
The table below illustrates compounds that were synthesized in accordance with the present invention. Detailed synthesis are provided in the Examples.
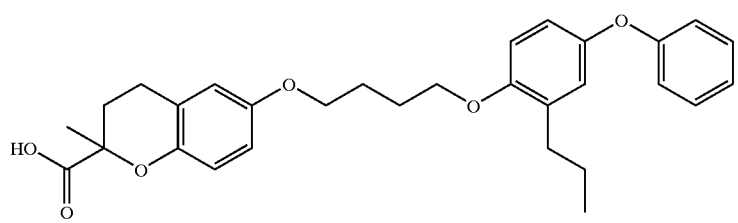
Example 16
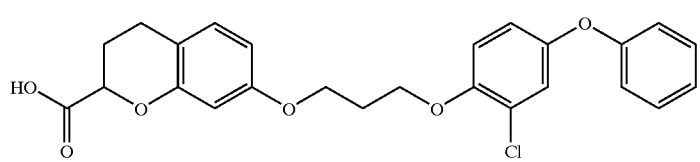
Example 17
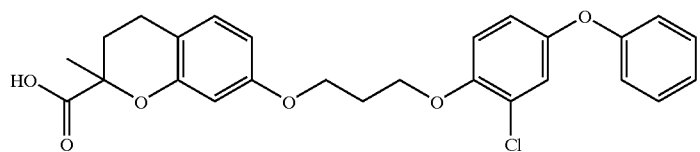
Example 18
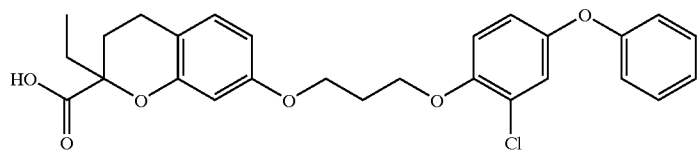
Example 19
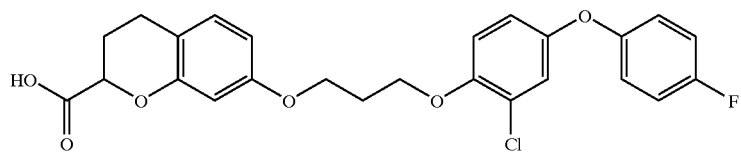
Example 20
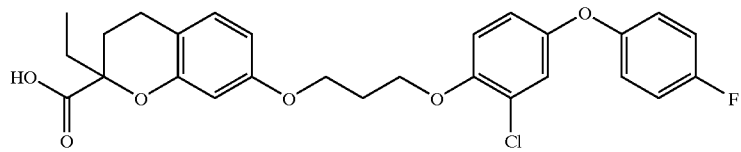
Example 21
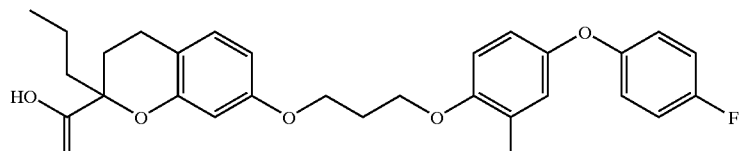
Example 22
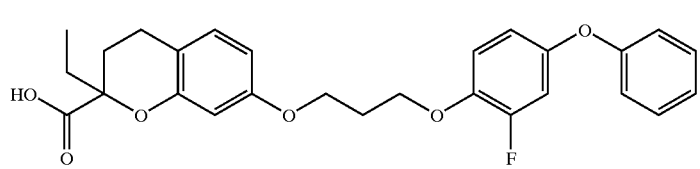
Example 23

TABLE OF COMPOUNDS
The table below illustrates compounds that were synthesized in accordance with the present invention. Detailed synthesis are provided in the Examples.
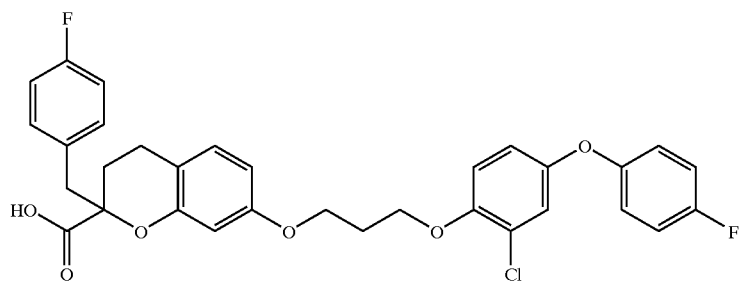
Example 24
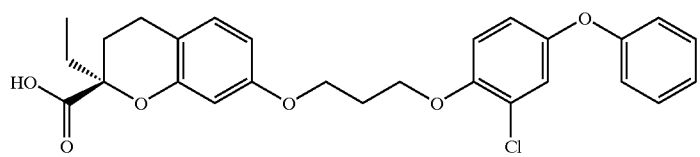
Example 25
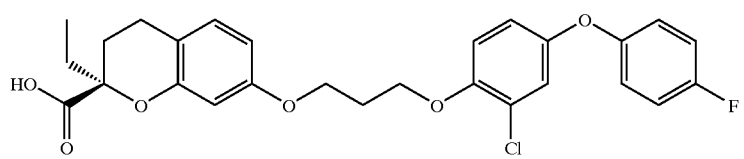
Example 26
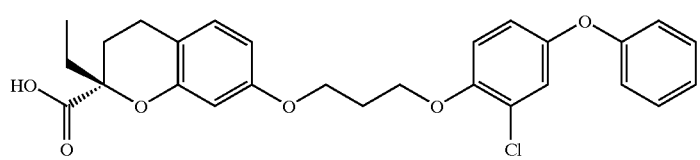
Example 27
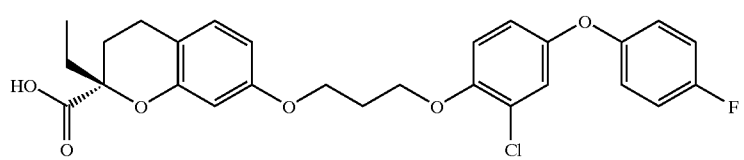
Example 28
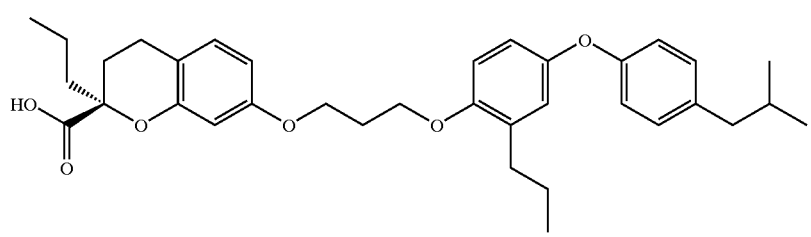
Example 29

SYNTHETIC METHODS

The process for making the compounds of the instant invention is generally described in Scheme 1 shown below.

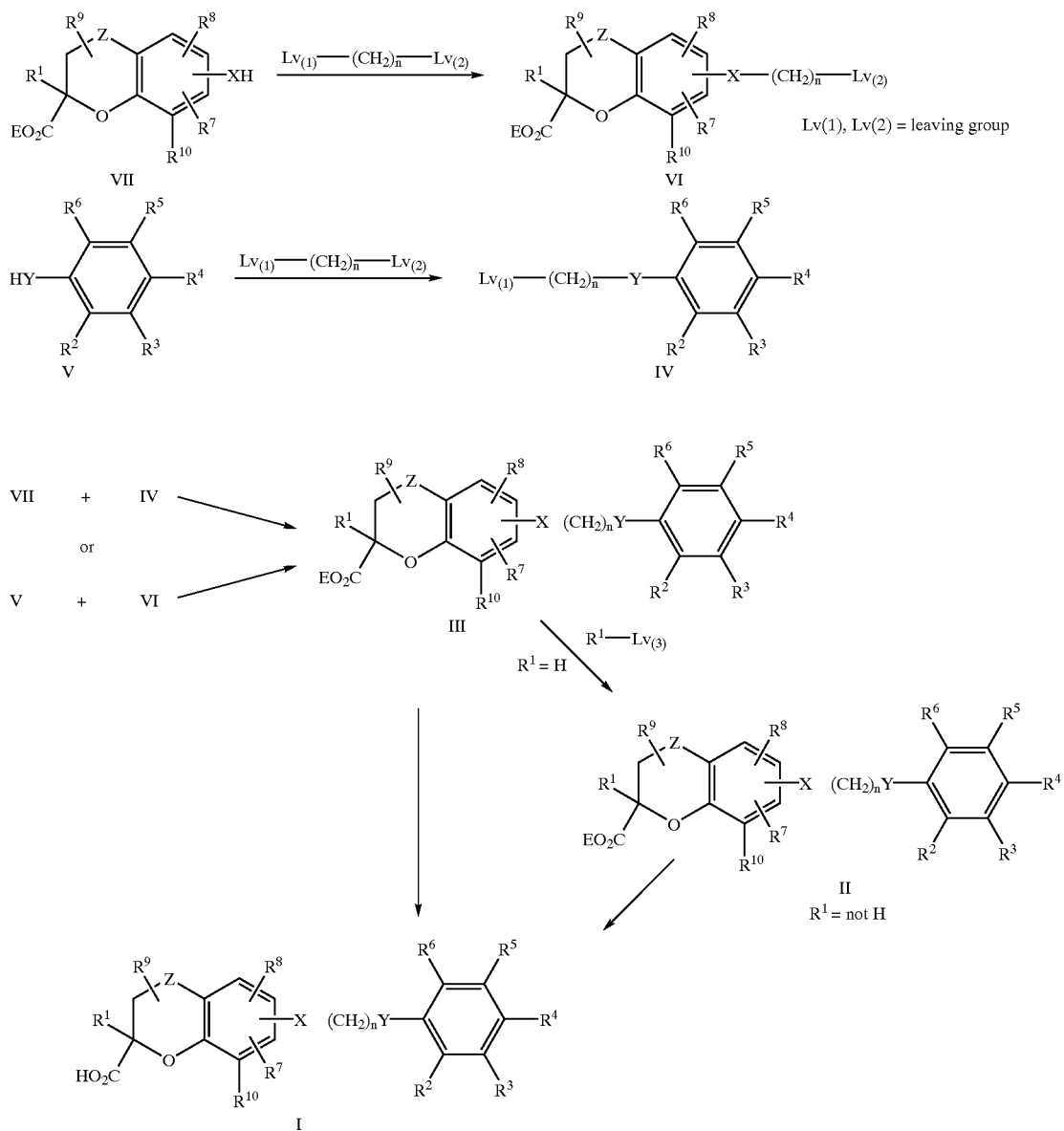

Scheme 1

The appropriately substituted benzopyran carboxylate of formula III (E is alkyl or aryl, for example, a methyl or ethyl group) may be synthesized by the coupling of compounds having formulae VII and IV, or by the coupling of compounds having formulae V and VI, where coupling is carried out in the presence of inorganic base (e.g. cesium carbonate) in DMF, or under standard Mitsunobu reaction condition (e.g. diiosopropyl azodicarboxylate and triphenyl phosphine) in dichloromethane. $Lv_{(1)}$ and $LV_{(2)}$ are leaving groups well-known in the art, and preferably are independently selected from halogen, preferably bromine, or sulfonate such as methanesulfonate or p-toluenesulfonate, or a hydroxyl group. Compounds having formulae VII and V may be commercially available, or prepared by published organic synthetic methods. The desired benzopyran carboxylic acid I may be synthesized by ester hydrolysis of the compound having formula III under aqueous basic (e. g. aq. NaOH) or acidic conditions.

Optionally, when the $R^1$ group in formula III is hydrogen, an $R^1$ group other than hydrogen may be introduced under standard ester enolate alkylation conditions (e.g. using sodium bis(trimethylsilyl)amide and $R^1$—$Lv_{(3)}$ in TEE solvent at low temperature, wherein $Lv_{(3)}$ is a leaving group, preferably iodine or bromine, to give a compound having formula II. The desired benzopyran carboxylic acids I may be synthesized by ester hydrolysis of the compound having formula II under aqueous basic (e.g. aq. NaOH) or acidic conditions.

EXAMPLES

The following Examples are provided to illustrate the invention, including methods of making the compounds of the invention, and are not to be construed as limiting the invention in any manner. The scope of the invention is defined in the appended claims.

Example 1

7-(3-(2-Propyl-4-phenoxyphenoxy)propoxy)-chromane-2-carboxylic acid

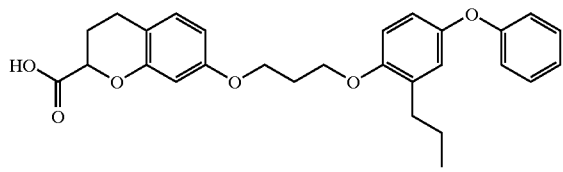

Step A: Ethyl-7-hydroxychromane-2-carboxylate

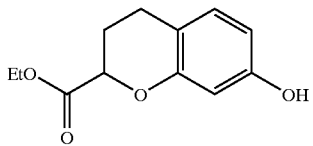

To a large hydrogenation vessel were added ethyl 7-hydroxychromone-2-carboxylate (=ethyl 7-hydroxy-4-oxo-4H-chromene-2-carboxylate) (675.4 g, 2.88 mol), EtOH 4 liters, conc. hydrochloric acid 40 ml. The resulting suspension was combined with 5% Pd/C 68 g, and subjected to hydrogenation condition (H$_2$, 40 psi, rt) overnight. The reaction mixture was filtered through a pad of celite to remove the catalyst. The filtrate was concentrated to give thick oily material, which solidified upon standing. Tan solid 630.1 g (98%).

$^1$H-NMR (500 MHz, CDCl$_3$): δ 6.89 (d, 1H, J=8.2 Hz), 6.46 (d, 1H, J=2.5 Hz), 6.4 (dd, 1H, J=2.5, 8.2 Hz), 4.9 (brs, 1H), 4.71 (dd, 1H, J=3.1, 7.5 Hz), 4.27 (q, 2H, J=7.3 Hz), 2.76 (m, 1H), 2.7 (m; 1H), 2.25 (m, 1H), 2.18 (m, 1H), 1.3 (t, 3H, J=7.2 Hz).

Step B: Ethyl 7-(3-(2-propyl-4-phenoxyphenoxy)propoxy)-chromane-2-carboxylate

To a 50 ml round-bottom flask were added ethyl 7-hydroxychromane-2-carboxylate (100 mg, 0.45 mmol), 4-(3-bromopropoxy)-3-propylphenyl phenyl ether (U.S. Pat. No. 6,008,237) (188 mg, 0.54 mmol), cesium carbonate (176 mg, 0.54 mmol), and DMF 3 ml. The resulting suspension was stirred at 70° C. for 5 hr. The solvent was removed under reduced pressure. The residue was diluted with AcOEt and water. The organic layer was separated. The aqueous layer was extracted twice with AcOEt. The combined organic layers were dried over anhydrous Na$_2$SO$_4$, filtered, concentrated, and chromatographed on silica gel. Eluting with 10% AcOEt/hexanes gave the title compound as a pale yellow oil 167 mg (76%).

$^1$H-NMR (500 MHz, CDCl$_3$): δ 7.3 (m, 2H), 7.04 (m, 1H), 6.92–6.96 (m, 3H), 6.87 (s, 1H), 6.83 (m, 2H), 6.54 (d, 1H, J=2.5 Hz), 6.5 (dd, 1H, J=2.5, 8.4 Hz), 4.7 (dd, 1H, J=3.5, 7.5 Hz), 4.28 (q, 2H, J=7.1 Hz), 4.15 (m, 4H), 2.8–2.65 (m, 2H), 2.56 (m, 2H), 2.23 (m, 3H), 2.18 (m, 1H), 1.60 (m, 2H), 1.31 (t, 3H, J=7.1 Hz), 0.93 (t, 3H, J=7.3 Hz).

Step C: 7-(3-(2-Propyl-4-phenoxyphenoxy)propoxy)-chromane-2-carboxylic acid

Ethyl 7-(3-(2-propyl-4-phenoxy)propoxy)-chromane-2-carboxylate (40 mg, 0.082 mmol) was dissolved in isopropanol 2 ml and 2N NaOH aq. 1 ml. The reaction was stirred at 70° C. overnight. The solvent was removed under reduced pressure, diluted with AcOEt and 2N HCl aq. The organic layer was separated. The aqueous layer was extracted twice with AcOEt. The combined organic layers were dried over anhydrous Na$_2$SO$_4$, filtered, and concentrated to give the title compound 38 mg as a pale yellow oil (quant.).

$^1$H-NMR (500 MHz, CDCl$_3$): δ 7.3 (m, 2H), 7.04 (tt, 1H, J=0.9, 7.3 Hz), 6.98–6.94 (m, 3H), 6.87 (s, 1H), 6.82 (m, 2H), 6.54 (m, 2H), 4.75 (dd, 1H, J=3.4, 8.3 Hz), 4.16 (t, 2H, J=6.2 Hz), 4.14 (t, 2H, J=6 Hz), 2.59–2.58 (m, 2H), 2.56 (m, 2H), 2.36 (m, 1H), 2.26 (p, 2H, J=6.1 Hz), 2.18 (m, 1H), 1.6 (m, 2H), 0.93 (t, 3H, J=7.3 Hz). ms: m/e=463 (M+1).

Example 2

7-(3-(2-Propyl-4-phenoxyphenoxy)propoxy)-2-propylchromane-2-carboxylic acid

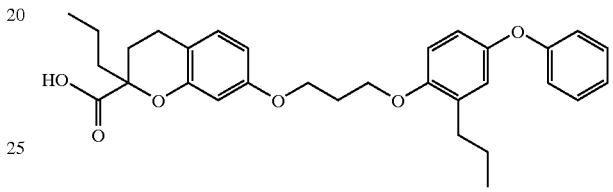

Step A: Ethyl 7-(3-(2-propyl-4-phenoxyphenoxy)propoxy)-2-propylchromane-2-carboxylate To a 2 ml THF solution of ethyl 7-(3-(2-propyl-4-phenoxyphenoxy)propoxy)-chromane-2-carboxylate (Example 1, Step B) (100 mg, 0.204 mmol) were added hexamethylphosphoramide (0.046 ml, 0.26 mmol) and sodium bis(trimethylsilyl)amide (1.0M THF solution) (0.265 ml, 0.265 mmol) upon cooling in a dry ice-acetone bath. After stirring at that temperature for 30min, to it was added iodopropane (0.06 ml, 6.2 mmol). The cooling bath was removed and the reaction mixture was gradually warmed to rt overnight. The solvent was removed under reduced pressure, diluted with AcOEt and water. The organic layer was separated. The aqueous layer was extracted twice with AcOEt. The combined organic layers were dried over anhydrous Na$_2$SO$_4$, filtered, concentrated, and chromatographed on silica gel. Elution with 5% AcOEt/hexanes gave the title compound as a clear oil 33 mg (30%).

$^1$H-NMR (500 MHz, CDCl$_3$): δ 7.3 (m, 2H), 7.04 (tt, 1H, J=0.9, 7.4 Hz), 6.95 (m, 2H), 6.9 (d, 1H, J=8.5 Hz), 6.87 (s, 1H), 6.82 (m, 2H), 6.53 (d, 1H, J=2.5 Hz), 6.46 (dd, 1H, J=0.45, 2.5 Hz), 4.16 (m, 6H), 2.7–2.55 (m, 4H), 2.27 (p, 2H, J=6.1 Hz), 1.95–1.88 (m, 2H), 1.85–1.8 (m, 1H), 1.7–1.6 (m, 3H), 1.37 (m, 1H), 1.22 (t, 3H, J=7.3 Hz), 0.97 (t, 3H, J=7.1 Hz), 0.94 (t, 3H, J=7.6 Hz).

Step B: 7-(3-(2-Propyl-4-phenoxyphenoxy)propoxy)-2-propylchromane-2-carboxylic acid The title compound was prepared from ethyl 7-(3-(2-propyl-4-phenoxyphenoxy)propoxy)-2-propylchromane-2-carboxylate following the procedure described in Example 1, Step C.

$^1$H-NMR (500 MHz, CDCl$_3$): δ 7.3 (m, 2H), 7.0 (tt, 1H, J=0.9, 7.4 Hz), 6.95 (m, 3H), 6.87 (s, 1H), 6.83 (m, 2H), 6.52 (m, 2H), 4.17 (t, 2H, J=6 Hz), 4.14 (t, 2H, J=6 Hz), 2.72 (m, 2H), 2.58 (m, 2H), 2.3 (m, 3H), 2.05–1.8 (m, 3H), 1.6 (m, 3H), 1.4 (m, 1H), 0.96 (t, 3H, J=7.5 Hz), 0.93 (t, 3H, J=7.3 Hz). ms: m/e=505 (M+1).

Example 3

7-(4-(2-Propyl-4-phenoxyphenoxy)butoxy)-chromane-2-carboxylic acid

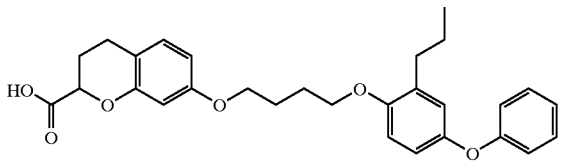

The title compound was prepared following the procedure in Example 1, Steps A-C using 4-(4-bromobutoxy)-3-propylphenyl phenyl ether (U.S. Pat. No. 6,008,237) instead of 4-(3-bromopropoxy)-3-propylphenyl phenyl ether.

$^1$H-NMR (500 MHz, CDCl$_3$): δ 7.31 (m, 2H), 7.04 (t, 1H, J=7.4 Hz), 6.96 (m, 3H), 6.88 (d, 1H, J=2.5 Hz), 6.84–6.79 (m, 2H), 6.53 (m, 2H), 4.73 (dd, 1H, J=3.2, 8.7 Hz), 4.03 (m, 4H), 2.85 (m, 1H), 2.75 (m, 1H), 2.59 (m, 2H), 2.34 (m, 1H), 2.15 (m, 1H), 2.0 (m, 1H), 1.6 (sext, 2H, J=7.5 Hz), 0.94 (t, 3H, J=7.4 Hz). ms: m/e=477 (M+1).

Example 4

7-(4-(2-Propyl-4-phenoxyphenoxy)butoxy)-2-methylchromane-2-carboxylic acid

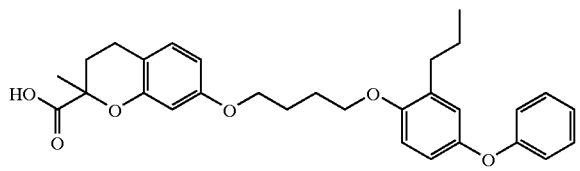

Ethyl 7-(4-(2-propyl-4-phenoxyphenoxy)butoxy)-chromane-2-carboxylate, which was prepared as described in Example 3, was treated as described in Example 2, Step A employing iodomethane instead of iodopropane to give ethyl 7-(4-(2-Propyl-4-phenoxyphenoxy)butoxy)-2-methylchromane carboxylate. This material was treated as described in Example 1, Step C to give the title compound.

$^1$H-NMR (500 MHz, CDCl$_3$): δ 7.31 (m, 2H), 7.04 (t, 1H, J=7.4 Hz), 6.98–6.94 (m, 3H), 6.87 (d, 1H, J=2.6 Hz), 6.84–6.79 (m, 2H), 6.55–6.49 (m, 2H), 4.02 (m, 4H), 2.73 (m, 1H), 2.59 (m, 2H), 2.37 (m, 1H), 2.0 (m, 6H), 1.65 (s, 3H), 1.6 (sext. 2H, J=7.5 Hz), 0.94 (t, 3H, J=7.4 Hz). ms: m/e=491 (M+1).

Example 5

7-(3-(2-Propyl-4-(4-chlorophenoxy)phenoxy)propoxy)-2-ethylchromane-2-carboxylic acid

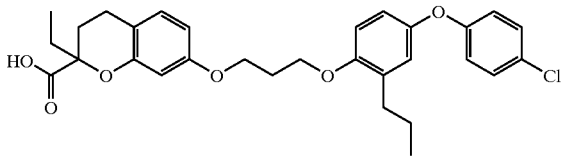

Step A: Ethyl 7-(3-benzyloxypropoxy)-chromane-2-carboxylate

To a 200 ml acetone solution of ethyl 7-hydroxychromane-2-carboxylate (9.18 g, 41.3 mmol) was added benzyl 3-bromopropyl ether (14.2 g, 62.0 mmol), powdered potassium carbonate (11.4 g, 82.5 mmol), and tetrabutylammonium iodide (1.53 g, 4 mmol). The resulting suspension was heated to reflux overnight. Acetone was removed under reduced pressure, diluted with AcOEt and sat. NH$_4$Claq. The organic layer was separated. The aqueous layer was extracted with AcOEt twice. The combined organic layers were dried over anhydrous Na$_2$SO$_4$, filtered, concentrated, and chromatographed on slica gel eluting with 10% AcOEt/hexanes to give the title compound 10.1 g (66%).

$^1$H-NMR (500 MHz, CDCl$_3$): δ 7.36–7.27 (m, 5H), 6.92 (d, 1H, J=8.2 Hz), 6.52 (d, 1H, J=2.5 Hz), 6.48 (dd, 1H, J=2.6, 8.3 Hz), 4.7 (dd, 1H, J=3.4, 7.6 Hz), 4.54 (s, 2H), 4.27 (dq, 2H, J=1.2, 7.2 Hz), 4.06 (t, 2H, J=6.2 Hz), 3.66 (t, 2H, J=6.2 Hz), 2.8–2.65 (m, 2H), 2.23 (m, 1H), 2.18 (m, 1H), 2.08 (p, 2H, J=6.2 Hz), 1.31 (t, 3H, J=7.2 Hz).

Step B: Ethyl 7-(3-benzyloxypropoxy)-2-ethylchromane-2-carboxylate

The title compound was prepared from ethyl 7-(3-benzyloxypropoxy)-chromane-2-carboxylate following the procedure described in Example 2, Step A employing iodoethane instead of iodopropane.

$^1$H-NMR (500 MHz, CDCl$_3$): δ 7.35 (m, 4H), 7.3 (m, 1H), 6.89 (d, 1H, J=8.3 Hz), 6.53 (d, 1H, J=2.6 Hz), 6.45 (dd, 1H, J=2.5, 8.2 Hz), 4.54 (s, 2H), 4.19 (m, 2H), 4.07, (m, 2H), 3.67 (t, 2H, J=6.3 Hz), 2.66–2.61 (m, 2H), 2.33 (m, 1H), 2.09 (p, 2H, J=6.2 Hz), 2.0 (m, 1H), 1.91 (m, 2H), 1.23 (t, 3H, J=7.1 Hz), 1.04 (t, 3H, J=7.4 Hz).

Step C: Ethyl 7-(3-hydroxypropoxy)-2-ethylchromane-2-carboxylate

To an 80 ml ethanol solution of ethyl 7-(3-benzyloxypropoxy)-2-ethylchromane-2-carboxylate (3.76 g, 9.5 mmol) was added water 4 ml and 10% Pd/C 300 mg. This solution was placed in a Parr shaker and was shaken under hydrogen atmosphere (50 psi) overnight. The catalyst was removed by filtration through a pad of celite. The filtrate was concentrated and chromatographed on silica gel. Elution with 30% AcOEt/hexanes gave the title compound 2.88 g as colorless syrup (quant.).

$^1$H-NMR (500 MHz, CDCl$_3$): δ 6.90 (d, 1H, J=8.2 Hz), 6.53 (d, 1H, J=2.5 Hz), 6.45 (dd, 1H, J=2.5, 8.4 Hz), 4.19 (m, 2H), 4.11 (m, 2H), 3.86 (t, 2H, J=6 Hz), 2.66–2.61 (m, 2H), 2.33 (m, 1H), 2.04 (p, 2H, J=6 Hz), 1.9 (m, 3H), 1.6 (brs, 1H), 1.23 (t, 3H, J=7.1 Hz), 1.04 (t, 3H, J=7.6 Hz).

Step D: Ethyl 7-(3-bromopropoxy)-2-ethylchromane-2-carboxylate

To a 100 ml CH$_3$CN solution of ethyl 7-(3-hydroxypropoxy)-2-ethylchromane-2-carboxylate (2.88 g, 9.4 mmol) was added triphenylphosphine (3.21 g, 12.2 mmol) and carbon tetrabromide (4.05 g, 12.2 mmol) upon cooling in an ice-water bath. After stirring at rt for 1 hr, the solvent was removed under reduced pressure. The residue was suspended in dichloromethane and was charged onto a silica gel column. Elution with 10% AcOEt/hexanes gave the title compound 3.36 g (96%).

$^1$H-NMR (500 MHz, CDCl$_3$): δ 6.9 (d, 1H, J=8.5 Hz), 6.53 (d, 1H, J=2.5 Hz), 6.45 (dd, 1H, J=2.5, 8.2 Hz), 4.19 (m, 2H), 4.08 (m, 2H), 3.6 (t, 2H, J=6.5 Hz), 2.65 (m, 2H), 2.31 (m, 3H), 2.0 (m, 1H), 1.91 (m, 2H), 1.23 (t, 3H, J=7.1 Hz), 1.04 (t, 3H, J=7.5 Hz).

Step E: 7-(3-(2-Propyl-4-(4-chlorophenoxy)phenoxy)propoxy)-2-ethylchromane-2-carboxylic acid The title compound was prepared from ethyl 7-(3-bromopropoxy)-2-ethylchromane-2-carboxylate and 2-propyl-4-(4-chlorophenoxy)phenol (U.S. Pat. No. 6,008,237) following the procedures described in Example 1, Steps B–C.

¹H-NMR (500 MHz, CDCl₃): δ 7.25 (m, 2H), 6.96 (d, 1H, J=8 Hz), 6.88 (m, 2H), 6.83 (m, 3H), 6.52 (m, 2H), 4.17 (t, 2H, J=6.0 Hz), 4.14 (t, 2H, J=6.1 Hz), 2.7 (m, 2H), 2.58 (m, 2H), 2.3 (m, 3H), 2.0 (m, 2H), 1.94 (m, 1H), 1.6 (sext. 2H, J=7.5 Hz), 1.06 (t, 3H, J=7.5 Hz), 0.93 (t, 3H, J=7.4 Hz). ms: m/e=525 (M+1).

Example 6

7-(3-(2-Propyl-4-(4-fluorophenoxy)phenoxy) propoxy)-2-ethylchromane-2-carboxylic acid

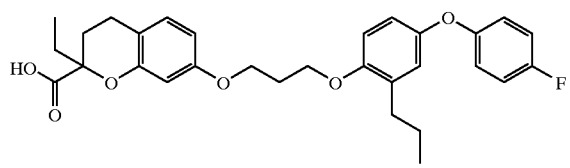

Following the procedures described in Example 5, the title compound was prepared using 2-propyl-4-(4-fluorophenoxy)phenol (U.S. Pat. No. 6,008,237) instead of 2-propyl-4-(4-chlorophenoxy)phenol.

¹H-NMR (500 MHz, CDCl₃): δ 6.98 (m, 3H), 6.91 (m, 2H), 6.8 (m, 3H), 6.52 (m, 2H), 4.16 (t, 2H, J=6.1 Hz), 4.13 (t, 2H, J=6 Hz), 2.57 (m, 2H), 2.55 (m, 2H), 2.3 (mm, 1H), 2.27 (p, 2H, J=6.1 Hz), 1.60 (m, 3H), 1.59 (sext. 2H, J=7.5 Hz), 1.06 (t, 3H, J=7.5 Hz), 0.93 (t, 3H, J=7.4 Hz). ms: m/e=509 (M+1).

Example 7

7-(3-(2-Propyl-4-(4-methoxyphenoxy)phenoxy) propoxy)-2-ethylchromane-2-carboxylic acid

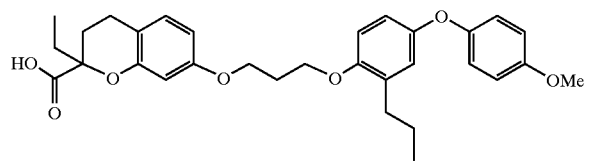

Following the procedures described in Example 5, the title compound was prepared using 2-propyl-4-(4-methoxyphenoxy)phenol (U.S. Pat. No. 6,008,237) instead of 2-propyl-4-(4-chlorophenoxy)phenol.

¹H-NMR (500 MHz, CDCl₃): δ 6.97–6.91 (m, 3H), 6.86 (m, 2H), 6.82–6.74 (m, 3H), 6.52 (m, 2H), 4.16 (t, 2H, J=6.2 Hz), 4.12 (t, 2H, J=6 Hz), 3.8 (s, 3H), 2.7 (m, 2H), 2.55 (m, 2H), 2.3 (m, 1H), 2.25 (pent., 2H, J=6.1 Hz), 1.95 (m, 3H), 1.59 (sext., 2H, J=7.6 Hz), 1.06 (t, 3H, J=7.3 Hz), 0.93 (t, 3H, J=7.3 Hz). ms; m/e=521 (M+1).

Example 8

7-(3-(4-Phenoxyphenoxy)propoxy)-2-ethylchromane-2-carboxylic acid

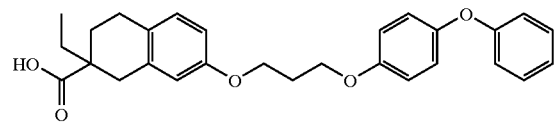

Following the procedures described in Example 5, the title compound was prepared using 4-phenoxyphenol instead of 2-propyl-4-(4-chlorophenoxy)phenol.

¹H NMR (500 MHz, CDCl₃): δ 7.31 (m, 2H), 7.05 (t, 1H, J=7.4 Hz), 6.97 (m, 5H), 6.90 (m, 2H), 6.52 (m, 2H), 4.14 (t, 4H, J=6.1 Hz), 2.71 (m, 2H), 2.33 (dt, 1H, J=5.3, J=13.5 Hz), 2.26 (p, 2H, J=6 Hz), 1.9–2.05 (m, 3H), 1.06 (t, 3H, J=7.4 Hz). ms: m/e=449 (M+1).

Example 9

7-(3-(2-Propyl-4-(4-methylsulfonylphenoxy) phenoxy)propoxy)-2-ethylchromane-2-carboxylic acid

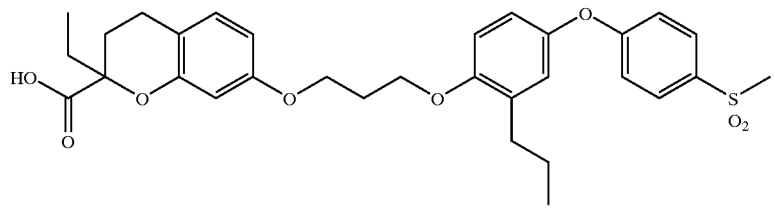

Following the procedures described in Example 5, the title compound was prepared using 2-propyl-4-(4-methylsulfonylphenoxy)phenol (U.S. Pat. No. 6,008,237) instead of 2-propyl-4-(4-chlorophenoxy)phenol.

¹H NMR (500 MHz, CDCl₃): δ 7.86 (d, 2H, J=8.9 Hz), 7.03 (d, 2H, J=9 Hz), 6.96 (d, 1H, J=8.0 Hz), 6.88 (s, 3H), 6.52 (m, 2H), 4.16 (m, 4H), 3.06 (s, 3H), 2.72 (m, 2H), 2.6 (m, 2H), 2.3 (m, 3H), 2.05–1.9 (m, 3H), 1.61 (sext, 2H, J=7.4 Hz), 1.06 (t, 3H), J=7.4 Hz), 0.94 (t, 3H, J=7.3 Hz). Ms: m/e=537 (M+1).

Example 10

7-(3-(2-Propyl-4-(4-isobutoxyphenoxy)phenoxy)propoxy)-2-ethylchromane-2-carboxylic acid

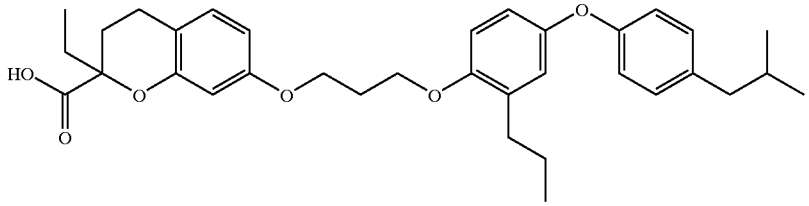

Following the procedures described in Example 5, the title compound was prepared using 2-propyl-4-(4-isobutylphenoxy)phenol (U.S. Pat. No. 6,008,237) instead of 2-propyl-4-(4-chlorophenoxy)phenol.

$^1$H NMR (500 MHz, CDCl$_3$): δ 7.07 (dd, 2H, J=1.6, J=7.4 Hz), 6.96 (d, 1H, J=8.1 Hz), 6.87 (m, 3H), 6.81 (m, 2H), 6.53 (m, 2H), 4.17 (t, 2H, J=6.2 Hz), 4.13 (t, 2H, J=6 Hz), 2.72 (m, 2H), 2.57 (m, 2H), 2.45 (d, 2H, J=7.1), 2.35 (m, 1H), 2.25 (p, 2H, J=6.0 Hz), 1.8–2.05 (m, 4H), 1.6 (sext, 2H, J=7.5 Hz), 1.05 (m, 3H), 0.9 (m, 9H). ms: m/e=547 (M+1).

Example 11

7-(2-(2-Propyl-4-phenoxyphenoxy)ethoxy)-2-ethylchromane-2-carboxylic acid

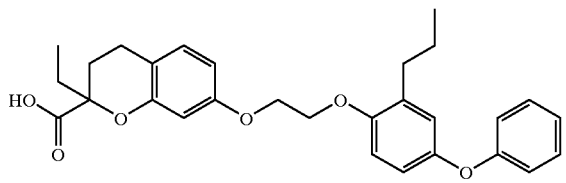

Step A: Ethyl 7-(2-bromoethoxy)-chromane-2-carboxylate

To a 60 ml dichloromethane solution of ethyl 7-hydroxychromane-2-carboxylate (1.32 g, 5.9 mmol), 2-bromoethanol (0.84 ml, 11.9 mmol), and triphenylphosphine (3.12 g, 11.9 mmol) was added diisopropyl azodicarboxylate (2.34 ml, 11.9 mmol) dropwise upon cooling in an ice-water bath. After stirring at rt overnight, the solvent was removed under reduced pressure, and the residue was chromatographed on silica gel eluting with 10% AcOEt/hexanes to give the title compound 1.27 g (65%).

$^1$H NMR (500 MHz, CDCl$_3$): δ 6.94 (d, 1H, J=8.3 Hz), 6.5 (m, 2H), 4.7 (dd, 1H, J=3.5, J=7.6 Hz), 4.27 (q, 2H, J=7.1 Hz), 4.27 (m, 2H), 3.62 (t, 2H, J=6.4 Hz), 2.77 (m, 1H), 2.7 (m, 1H), 2.26 (m, 1H), 2.18 (m, 1H), 1.31 (t, 3H, J=7.2 Hz).

Step B: 7-(2-Bromoethoxy)-2-ethylchromane-2-carboxylate

The title compound was prepared from ethyl 7-(2-bromoethoxy)-chromane-2-carboxylate following the procedure described in Example 2, Step A employing iodoethane instead of iodopropane.

$^1$H NMR (500 MHz, CDCl$_3$): δ 6.91 (d, 1H, J=8.5 Hz), 6.52 (d, 1H, J=2.6 Hz), 6.475 (dd, 1H, J=2.5, J=8.2 Hz), 4.27 (m, 2H), 4.2 (m, 2H), 3.63 (t, 2H, J=6.3 Hz), 2.6–2.75 (m, 2H), 2.33 (ddd, 1H, J=3.5, J=5.4, J=13.6 Hz), 2.0 (m, 1H), 1.9 (m, 2H), 1.05 (t, 3H, J=7.4 Hz), 0.94 (t, 3H, J=7.3 Hz).

Step C: Ethyl 7-(2-(2-propyl-4-phenoxy)ethoxy)-2-ethylchromane-2-carboxylate

To a 1 ml DMF solution of 7-(2-bromoethoxy)-2-ethylchromane-2-carboxylate (43 mg, 0.12 mmol) was added 2-propyl-4-phenoxyphenol (30.2 mg, 0.13 mmol), and cesium carbonate (43 mg, 0.13 mmol). The resulting suspension was heated to 70° C. for 5 hr. The solvent was removed under reduced pressure, then diluted with AcOEt and water. The organic layer was separated, the aqueous layer was extracted twice with AcOEt. The combined organic layers were dried over anhydrous Na$_2$SO$_4$, filtered, concentrated, chromatographed on silica gel to give the title compound 16 mg as a clear oil.

$^1$H NMR (500 MHz, CDCl$_3$): δ 7.31 (m, 2H), 7.05 (t, 1H, J=7.4 Hz), 6.97 (m, 2H), 6.92 (d, 1H, J=5.5), 6.88 (m, 1H), 6.85 (m, 2H), 6.58 (d, 1H, J=2.5 Hz), 6.52 (dd, 1H, J=2.5, J=8.5 Hz), 4.3 (m, 4H), 4.2 (m, 2H), 2.65–2.75 (m, 2H), 2.6 (m, 2H), 2.34 (ddd, 1H, J=3.5, J=5.4, J=13.3 Hz), 2.01 (m, 1H), 1.92 (m, 2H), 1.61 (sext, 2H, J=7.6 Hz), 1.24 (t, 3H, J=7.1 Hz), 1.05 (t, 3H, J=7.4 Hz), 0.93 (t, 3H, J=7.4 Hz).

Step D: 7-(2-(2-Propyl-4-phenoxy)ethoxy)-2-ethylchromane-2-carboxylic acid

Following the procedure described in Example 1, Step C, ethyl 7-(2-(2-propyl-4-phenoxyphenoxy)ethoxy)-2-ethylchromane-2-carboxylate was converted to the title compound.

$^1$H NMR (500 MHz, CDCl$_3$): δ 7.32 (t, 2H, J=7.7), 7.05 (t, 1H, J=7.3 Hz), 6.96 (d, 3H, J=8 Hz), 6.86 (m, 3H), 6.55 (m, 2H), 4.31 (m, 4H), 2.73 (m, 2H), 2.58 (m, 2H), 2.33 (m, 1H), 1.98 (m, 3H), 1.61 (sext, 2H, J=7.4 Hz), 1.08 (t, 3H, J=7.3 Hz), 0.93 (t, 3H, J=7.3 Hz). ms: m/e=477 (M+1).

Example 12

7-(2-(2-Propyl-4-(4-methylsulfonylphenoxy)phenoxy)ethoxy)-2-ethylchromane-2-carboxylic acid

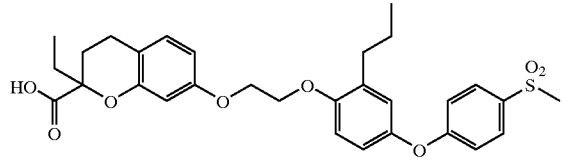

The title compound was prepared following the procedure described in Example 11 employing 2-propyl-4-(4-methylsulfonyl)phenoxyphenol (U.S. Pat. No. 6,008,237) instead of 2-propyl-4-phenoxyphenol.

$^1$H NMR (500 MHz, CDCl$_3$): δ 7.87 (d, 2H, J=8.9 Hz), 7.04 (d, 2H, J=8.7 Hz), 6.97 (d, 1H, J=8.2 Hz), 6.90 (m, 3H), 6.57 (d, 1H, J=2.2), 6.55 (dd, 1H, J=2.4), 4.32 (m, 4H), 3.06 (s, 3H), 2.72 (m, 2H), 2.6 (m, 2H), 2.33 (m, 1H), 1.9–2.05 (m, 1H), 1.62 (sext, 2H, J=7.5), 1.08 (t, 3H, J-7.3), 0.93 (t, 3H, J=7.3). ms: m/e=556(M+1).

Example 13

6-(3-(2-Propyl-4-phenoxyphenoxy)propoxy)-2-chromane-2-carboxylic acid

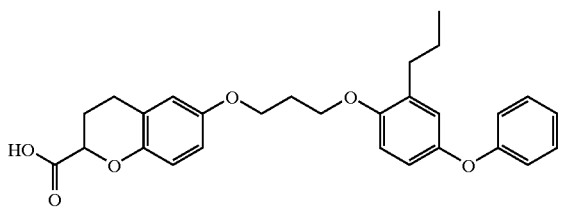

Ethyl 6-hydroxychromone-2-carboxylate (Baker, G.; Ellis, G. P. *J. Chem. Soc.* (C), 1970, 2230.) was treated as described in Example 1, Steps A–C to give the title compound.

$^1$NMR (500 MHz, CD$_3$OD): δ 7.27 (m, 2H), 7.01 (t, 1H, J=7.4 Hz), 6.89 (m, 3H), 6.77 (m, 3H), 6.69 (dd, 1H, J=2.8, J=8.8 Hz), 6.63 (d, 1H, J=2.8 Hz), 4.62 (m, 1H), 4.13 (m, 4H), 2.82 (m, 1H), 2.72 (m, 1H), 2.55 (m, 2H), 2.25 (m, 1H), 2.22 (p, 2H), J=6 Hz), 2.01 (m, 1H), 1.55 (sext, 2H, J=7.5), 0.89 (t, 3H, J=7.3). ms: m/e=463 (M+1).

Example 14

6-(3-(2-Propyl-4-phenoxyphenoxy)propoxy)-2-methylchromane-2-carboxylic acid

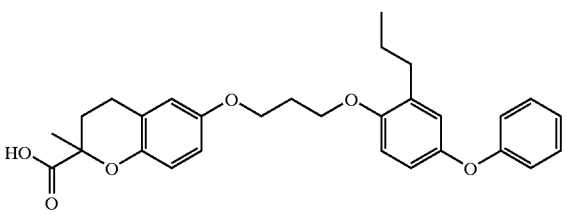

The title compound was prepared from ethyl 6-(3-(2-propyl-4-phenoxyphenoxy)propoxy)-chromane-2-carboxylate (Example 13) following the procedures described in Example 2, Step A, employing iodomethane instead of iodopropane, and subsequently hydrolyzed following the procedure in Example 1, Step C.

$^1$H NMR (500 MHz, CD$_3$OD): δ 7.27 (t, 2H, J=7.9 Hz), 7.0 (t, 1H, J=7.2 Hz), 6.88 (m, 3H), 6.79 (m, 2H), 6.73 (d, 1H, J=8.7 Hz), 6.68 (dd, 1H, J=2.8, J=8.7 Hz), 6.61 (d, 1, J=2.2 Hz), 4.1 (m, 4H), 2.7 (m, 2H), 2.55 (t, 2H, J=7.4 Hz), 2.35 (m, 1H), 2.2 (p, 2H, J=6.1 Hz), 1.85 (m, 1H), 1.55 (m, 5H), 0.881 (t, 3H, J=7.4 Hz). ms: m/e=477 (M+1).

Example 15

6-(4-(2-Propyl-4-phenoxyphenoxy)butoxy)-2-chromane-2-carboxylic acid

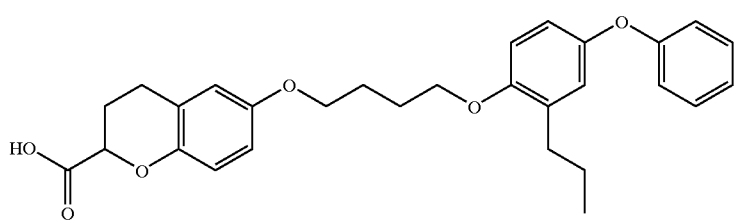

Title compound was prepared following the procedure described in Example 13 using 4-(4-bromobutoxy)-3-propylphenyl ether (U.S. Pat. No. 6,008,237) instead of 4-(3-bromopropoxy)-3-propylphenyl phenyl ether.

$^1$H NMR (500 MHz, CD$_3$OD): δ 7.275 (m, 2H), 7.01 (t, 1H, J=7.4 Hz), 6.88 (m, 3H), 6.79–6.74 (m, 3H), 6.67 (dd, 1H, J=2.8, J=8.7 Hz), 6.61 (d, 1H, J=2.7), 4.62 (m, 1H), 4.03 (t, 2H, J=5.6 Hz), 3.99 (t, 2H, J=5.7), 2.83 (m, 1H), 2.72 (m, 1H), 2.55 (m, 2H), 2.25 (m, 1H), 2.08 (m, 1H), 1.95 (m, 4H), 1.58 (sext, 2H, J=7.3 Hz), 0.9 (t, 3H, J=7.3 Hz). ms: m/e=477 (M+1).

Example 16

6-(4-(2-Propyl-4-phenoxyphenoxy)butoxy)-2-methyl-chromane-2-carboxylic acid

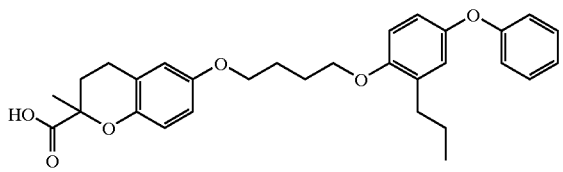

The title compound was prepared from ethyl 6-(4-(2-propyl-4-phenoxyphenoxy)butoxy)-chromane carboxylate following the procedures described in Example 2, Step A employing iodomethane instead of iodopropane, and subsequently the procedure in Example 1 Step C.

$^1$H NMR (500 MHz, CD$_3$OD): δ 7.27 (t, 2H, J=7.1 Hz), 7.01 (t, 1H, J=7.3 Hz), 6.88 (m, 3H), 6.77 (m, 2H), 6.73 (d, 1H, J=9.3 Hz), 6.67 (d, 1H, J=8.5 Hz), 6.59 (s, 1H), 4.0 (m, 4H), 2.7 (m, 2H), 2.55 (t, 2H, J=6 Hz), 2.35 (m,1H), 1.95 (m, 4H), 1.85 (m, 1H), 1.55 (s, 3H), 1.55 (m, 2H), 0.9 (t, 3H, J=6.8 Hz). ms: m/e=491 (M+1).

Example 17

7-(3-(2-Chloro-4-phenoxyphenoxy)propoxy)-chromane-2-carboxylic acid

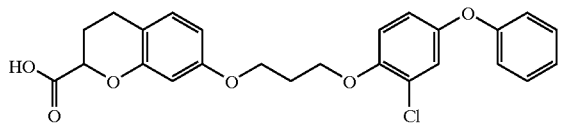

Step A: 2-Chloro-4-phenoxyphenol

To a 54 ml toluene solution of 4-phenoxyphenol (2 g, 10.7 mmol) and diisobutylamine (0.15 ml, 0.86 mmol) was added sulfuryl chloride (0.69 ml, 8.6 mmol). The mixture was heated to 70° C. for 3 hr. The solvent was removed under reduced pressure. The residue was diluted with AcOEt and aq sat. bicarbonate solution. The organic layer was separated, and the aqueous layer was extracted twice with AcOEt. The combined organic layers were dried over anhydrous $Na_2SO_4$, filtered, concentrated, and chromatographed on silica gel. Elution with 15% AcOEt/hexanes gave the title compound 2.3 g as colorless syrup (97%).

$^1$H NMR (500 MHz, $CDCl_3$): δ 7.352 (m, 2H), 7.116 (m, 1H), 7.059 (d, 1H), 7.024 (d, 1H), 6.988 (d, 2H), 6.923 (dd, 1H), 5.689 (s, 1H).

Step B: 3-Bromopropyl 2-chloro-4-phenoxyphenyl ether

To a 100 ml DMF solution of 2-chloro-4-phenoxyphenol (10 g, 45 mmol) were added 3-bromopropanol (8.2 ml, 91 mmol) and cesium carbonate (6.2 g, 50 mmol). The resulting suspension was heated to 70° C. for 7 hr. Solvent was removed under reduced pressure. The residue was diluted with AcOEt and water. The organic layer was separated. The aqueous layer was extracted twice with AcOEt. The combined organic layers were dried over anhydrous $Na_2SO_4$, filtered, concentrated, and chromatographed on silica gel. Elution with 30% AcOEt/hexanes gave 3-(2-chloro-4-phenoxyphenoxy)-propanol 11.96 g (95%). This material was dissolved in acetonitrile 200 ml. To it was added triphenylphosphine (18.5 g, 55.8 mmol) and carbon tetrabromide (16.9 g, 64.4 mmol). After stirring at rt for 1 hr, the solvent was removed, and the residue was chromatographed on silica gel. Elution with 5% THF/hexanes gave the title compound as colorless oil 10.9 g (74%).

$^1$H NMR (500 MHz, $CDCl_3$): δ 7.35 (m, 2H), 7.118 (m, 1H), 7.096 (d, 1H), 6.98 (m, 2H), 6.94 (s, 1H), 6.917 (dd, 1H), 4.173 (t, 2H), 3.695 (t, 2H), 2.383 (p, 2H).

Step C: 7-(3-(2-Chloro-4-phenoxyphenoxy)propoxy)-chromane-2-carboxylic acid

The title compound was prepared following the procedures described in Example 1, Steps B–C employing 3-bromopropyl 2-chloro-4-phenoxyphenyl ether instead of 4-(3-bromopropoxy)-3-propylphenyl phenyl ether.

$^1$H NMR (500 MHz, $CDCl_3$): δ 7.335 (m, 2H), 7.118 (m, 2H), 6.884–7.088 (m, 5H), 6.536 (m, 2H), 4.733 (dd, 1H), 4.192 (q, 4H), 2.769 (m, 2H), 2.356 (m, 1H), 2.297 (m, 2H), 2.176 (m, 1H). ms: m/e=455 (M+1).

Example 18

7-(3-(2-Chloro-4-phenoxyphenoxy)propoxy)-2-methylchromane-2-carboxylic acid

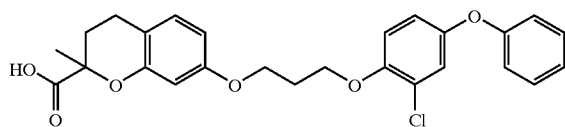

Step A: Ethyl 7-(3-(2-chloro-4-phenoxyphenoxy)propoxy)-2-methylchromane-2-carboxylate The title compound was prepared following the procedure described in Example 2 employing ethyl 7-(3-(2-chloro-4-phenoxyphenoxy)propoxy)-chromane-2-carboxylate (Example 17) instead of ethyl 7-(3-(2-propyl-4-phenoxyphenoxy)propoxy)-chromane-2-carboxylate, and iodomethane instead of iodopropane.

Step B: 7-(3-(2-Chloro-4-phenoxyphenoxy)propoxy)-2-methylchromane-2-carboxylic acid The title compound was prepared from ethyl 7-(3-(2-chloro-4-phenoxyphenoxy)propoxy)-2-methylchromane-2-carboxylate following the procedures described in Example 1, Step C.

$^1$H NMR (500 MHz, $CDCl_3$): δ 7.337 (m, 2H), 7.107 (d, 1H), 7.086 (d, 1H), 6.906–6.982 (m, 5H), 6.537 (dd, 1H), 6.52 (s, 1H), 4.195 (q, 4H), 2.727 (t, 2H), 2.353 (dt, 1H), 2.30 (p, 2H), 1.975 (dt 1H), 1.646 (s, 3H). ms: m/e=469 (M+1).

Example 19

7-(3-(2-Chloro-4-phenoxyphenoxy)propoxy)-2-ethylchromane-2-carboxylic acid

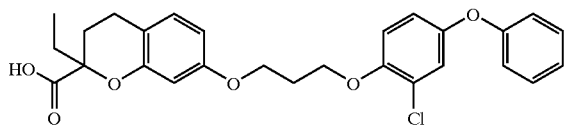

The title compound was prepared following the procedures described in Example 18 employing iodoethane instead of iodomethane.

$^1$H-NMR (500 MHz, $CDCl_3$): δ 7.34 (m, 2H), 7.09 (m, 2H), 6.99–6.89 (m, 5H), 6.54 (d, 1H, J=2 Hz), 6.51 (dd, 1H, J=1.6, 8.2 Hz), 4.2 (t, 2H, J=6 Hz), 4.19 (t, 2H), J=5.9 Hz), 2.71 (m, 2H), 2.3 (m, 1H), 2.3 (p, 2H, J=6 Hz), 2.05–1.9 (m, 3H), 1.06 (t, 3H, J=7.4 Hz). ms: m/e=483 (M+1).

Example 20

7-(3-(2-Chloro-4-(4-fluorophenoxy)phenoxy) propoxy)-chromane-2-carboxylic acid

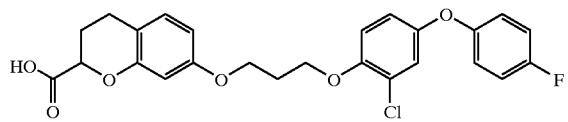

Step A: 3-Bromopropyl 2-chloro-4-(4-fluorophenoxy) phenyl ether

The title compound was prepared from 4-(4-fluorophenoxy)phenol following the procedure described in Example 17, Steps A–B.

$^1$H NMR (500 MHz, $CDCl_3$): δ 7.03–7.07 (m, 3H), 6.94–6.985 (m, 3H), 6.89 (dd, 1H), 4.18 (t, 2H), 3.70 (t, 2H), 2.38 (p, 2H). ms: m/e=359 (M+1).

Step B: 7-(3-(2-Chloro-4-(4-fluorophenoxy)phenoxy) propoxy)-chromane-2-carboxylic acid The title compound was prepared following the procedure described in Example 1, Steps B–C employing 3-bromopropyl 2-chloro-4-(4-fluorophenoxy)phenyl ether instead of 4-(3-bromopropoxy)-3-propylphenyl phenyl ether.

$^1$H NMR (500 MHz, $CDCl_3$): δ 7.05–7.01 (m, 2H), 6.98–6.91 (m, 5H), 6.86 (dd, 1H, J=2.7, J=8.9 Hz), 6.54 (m, 2H), 4.73 (dd, 1H, J=3.3, J=8.6 Hz), 4.2 (t, 2H, J=6 Hz), 4.19 (t, 2H, J=5.7 Hz), 2.85 (m, 1H), 2.75 (m, 1H), 2.38 (m, 1H), 2.3 (p, 2H, J=6 Hz), 2.17 (m, 1H). ms: m/e=473 (M+1).

Example 21

7-(3-(2-Chloro-4-(4-fluorophenoxy)phenoxy) propoxy)-2-ethylchromane-2-carboxylic acid

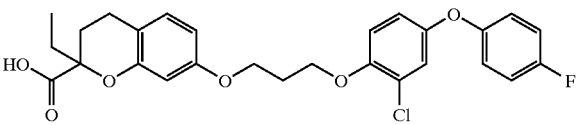

The title compound was synthesized following the procedure described in Example 2 employing ethyl 7-(3-(2-chloro-4-(4-fluorophenoxy)phenoxy)propoxy)-chromane-2- carboxylate (Example 20) instead of ethyl 7-(3-(2-propyl-4-phenoxyphenoxy)propoxy)-chromane-2-carboxylate, and iodoethane instead of iodopropane.

¹H-NMR (500 MHz, CDCl₃): δ 7.06–7.01 (m, 2H), 6.97–6.9 (m, 5H), 6.86 (dd, 1H, J=3, J=8.9 Hz), 6.55–6.51 (m, 2H), 4.2 (m, 4H), 2.7 (m, 2H), 2.3 (m 1H), 2.3 (p, 2H, J=6 Hz), 2.0 (m, 2H), 1.93 (m, 1H), 1.05 (t, 3H, J=7.3 Hz). ms: m/e=501 (M+1).

Example 22

7-(3-(2-Chloro-4-(4-fluorophenoxy)phenoxy)propoxy)-2-propylchromane-2-carboxylic acid

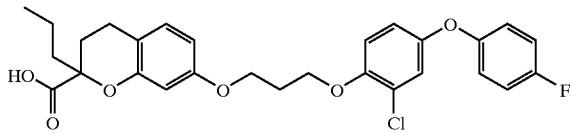

The title compound was synthesized following the procedure described in Example 2 employing ethyl 7-(3-(2-chloro-4-(4-fluorophenoxy)phenoxy)propoxy)-chromane-2-carboxylate (Example 20) instead of ethyl 7-(3-(2-propyl-4-phenoxyphenoxy)propoxy)-chromane-2-carboxylate.

¹H NMR (500 MHz, CDCl₃): δ 7.04 (m, 3H), 6.94 (m, 4H), 6.86 (m, 1H), 6.53 (m, 2H), 4.2 (m, 4H), 2.7 (m, 2H), 2.3 (m, 3H), 2.15–1.8 )m, 3H), 1.65 (m, 1H), 1.42 (m, 1H), 0.97 (t, 3H, J=7.2 Hz). ms: m/e=515 (M+1).

Example 23

7-(3-(2-Fluoro-4-phenoxyphenoxy)propoxy)-2-ethylchromane-2-carboxylic acid

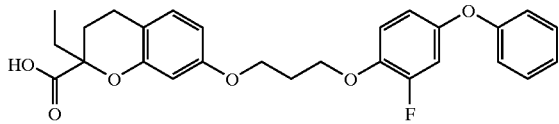

Step A: 2-Fluoro-4-phenoxyphenol

To a 250 ml dichloromethane solution of 4-phenoxyphenol (2 g, 10.7 mmol) was added 3,5-dichloro-1-fluoro-pyridinium triflate (4.14 g, 13.1 mmol). After heating to reflux for 1 hr, the solvent was removed, the crude product was diluted with AcOEt and sat. bicarb. solution. The organic layer was separated, dried over anhydrous Na₂SO₄, filtered, concentrated, and chromatographed on silica gel. Elution with 10% methy t-butyl ether/hexanes gave 312 mg of the title compound as a pale yellow oil.

¹H NMR (500 MHz, CDCl₃): δ 7.341 (m, 2H), 7.107 (mi, 1H), 6.977 (m, 3H), 6.824 (dd, 1H), 6.755 (m, 1H), 4.995 (s, 1H).

Step B: 7-(3-(2-Fluoro-4-phenoxyphenoxy)propoxy)-2-ethylchromane-2-carboxylic acid The title compound was prepared as described in Example 5, Step E employing 2-fluoro-4-phenoxyphenol instead of 2-propyl-4-(4-chlorophenoxy)phenol.

¹H NMR (500 MHz, CDCl₃): δ 7.345 (m, 2H), 7.11 (m, 1H), 6.932–7.001 (m, 4H), 6.818 (dd, 1H), 6.748 (m, 1H), 6.54 (d, 1H), 6.507 (dd, 1H), 4.175 (m, 4H), 2.712 (m, 2H), 2.324 (m, 1H), 2.277 (p, 2H), 1.91–2.072 (m, 3H), 1.069 (t, 3H). ms: m/e=467 (M+1).

Example 24

7-(3-(2-Chloro-4-(4-fluorophenoxy)phenoxy)propoxy)-2-(4-fluorophenylmehyl)-chromane-2-carboxylic acid

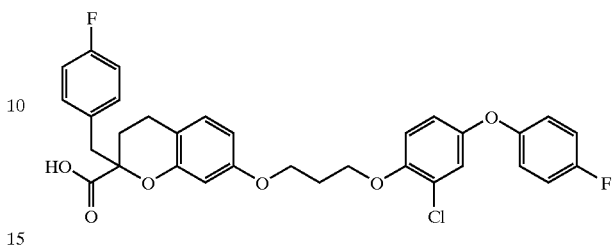

The title compound was prepared following the procedures described in Example 21 employing 4-fluorobenzyl bromide instead of iodoethane.

¹H NMR (500 MHz, CDCl₃): δ 7.288 (s, 1H), 7.24 (m, 2H), 6.93–7.06 (m, 8H), 6.875 (dd, 1H), 6.542–6.563 (m, 2H), 4.21 (m, 4H), 3.248 (d, 1H), 3.15 (d, 1H), 2.756 (m, 2H), 2.384 (m, 1H), 2.316 (p, 2H), 2.007 (m, 1H). ms: m/e=581 (M+1).

Example 25

(2R)-7-(3-(2-Chloro-4-phenoxyphenoxy)propoxy)-2-ethylchromane-2-carboxylic acid

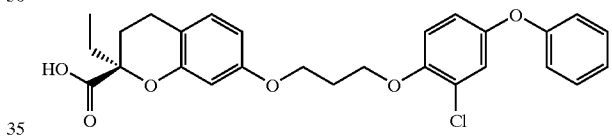

Step A: Ethyl 7-benzyloxychromane-2-carboxylate

To a 5 L acetone solution of ethyl 7-hydroxy-chromane-2-carboxylate (630.1 g, 2.84 mol) was added potassium carbonate powder (785 g, 5.68 mol) and benzyl bromide (405 ml, 3.41 mol). The resulting suspension was heated to reflux for 16 hr. The reaction mixture was filtered through a pad of celite. The filtrate was concentrated to give solid material, which was re-dissolved in AcOEt, washed with water to remove residual salt, dried over MgSO₄, filtered, concentrated to a small volume. Addition of hexanes caused precipitation of the title compound, which was collected by suction-filtration. The filtrate was triturated from dichloromethane-hexanes to give more precipitates. Finally the filtrate was concentrated and chromatographed on silica gel eluting with 20 to 80% dichloromethane/hexanes. Combination of all crops yielded the title compound 760.2 g as off-white solid (86%).

¹H NMR (500 MHz, CDCl₃): δ 7.33–7.457 (m, 5H), 6.955 (d, 1H), 6.621 (d, 1H), 6.576 (dd, 1H), 5.05 (s, 2H), 4.72 (q, 1H), 4.292 (q, 2H), 2.689–2.836 (m, 2H), 2.285 (m, 1H), 2.211 (m, 1H), 1.327 (t, 3H).

Step B: Ethyl 7-benzyloxy-2-ethylchromane-2-carboxylate

To a 320 ml anhydrous THF solution of ethyl 7-benzyloxychromane-2-carboxyate 14.6 g (46.6 mmol) were added hexamethylphosphoramide (10.5 ml, 60.4 mmol). Upon cooling in a dry ice-acetone bath, sodium bis(trimethylsilyl)amide (1.0M/THF) (60.5 ml, 60.5 mmol) was added via syringe over 15 min period. The resulting orange solution was stirred at that temperature for 30 min before iodoethane (18.6 ml , 233 mmol) was added via syringe. The reaction was slowly warmed to rt and stirred overnight. The solvent was removed under reduced pressure, and the residue was diluted with AcOEt and aqueous $NH_4Cl$ ($NH_4Cl$ 7.2 g/200 ml water). The organic layer was separated, and the aqueous layer was extracted with AcOEt twice. The combined organic layers were dried over anhydrous $Na_2SO_4$, filtered, concentrated, and chromatographed on silica gel eluting with 7.5% EtOAc/hexanes to give the title compound 15.2 g (96%).

$^1$H NMR (500 MHz, $CDCl_3$): δ 7.317–7.451 (m, 5H), 6.913 (d, 1H), 6.621 (d, 1H), 6.533 (dd, 1H), 5.041 (q, 2H), 4.195 (m, 2H), 2.625–2.67 (m, 2H), 2.334 (m, 1H), 2.003 (m, 1H) 1.915 (m, 2H), 1.232 (t, 3H), 1.045 (t, 3H).

Step C: 7-Benzyloxy-2-ethylchromane-2-carboxylic acid

To a 2 L isopropanol solution of ethyl 6-benzyloxy-2-ethylchromane-2-carboxylate (155 g, 0.455 mol) was added 1 L of aqueous 5N sodium hydroxide. This solution was heated to 70° C. overnight. Isopropanol was removed under reduced pressure. The residue was acidified with conc. hydrochloric acid 300 ml and 2N hydrochloric acid to pH 1. The acidic solution was extracted three times with AcOEt. The combined organic layers were dried over anhydrous $Na_2SO_4$, filtered, concentrated to give a yellow oil, which crystallized upon standing: 130 g (91%).

Step D: Resolution of the Racemate

1) Ester Formation with (R)-pantolactone

To a 1.1 L dichloromethane solution of 7-benzyloxy-2-ethylchromane-2-carboxylic acid (75 g, 0.24 mol), and (R)-pantolactone (100 g, 0.768 mol) were added EDC (55.5 g, 0.289 mol) and 4-(dimethylamino)pyridine (6.4 g, 0.054 mol). This solution was stirred at rt overnight. The solvent was removed under reduced pressure. The residue was diluted with AcOEt, washed with water and brine, dried over $MgSO_4$, filtered, and concentrated to give a yellow oil 137 g (crude).

2) Chromatographic Separation of the Diastereomers

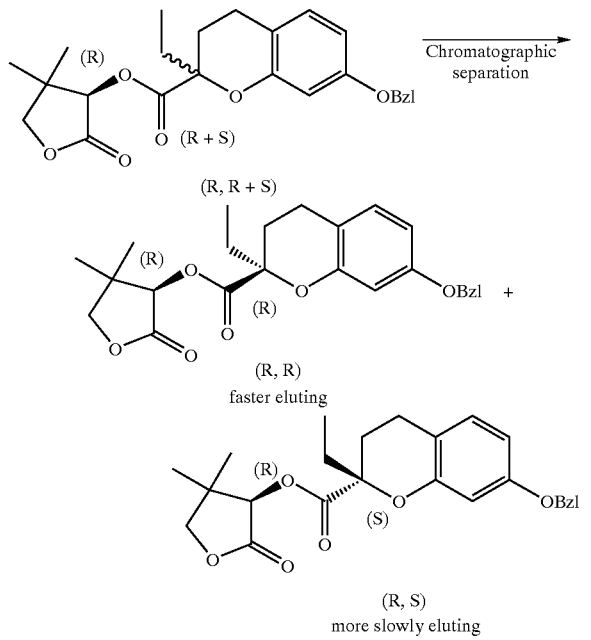

The crude ester obtained as described above was dissolved in hexanes and a small amount of dichloromethane and charged on a silica gel column. Elution with 10% THF/hexanes 48 liters, 12.5% THF/hexanes 64 liters, and 25% EtOAc/hexanes 4 liters gave the faster eluting (R, R) isomer 30.4 g (30%) as a colorless thick oil, more slowly eluting (R, S) isomer 34.5 g (34%) as a white solid, and the mixture of diastereomers 7 g (7%) as a yellow oil.

3) Determination of Absolute Stereochemistry

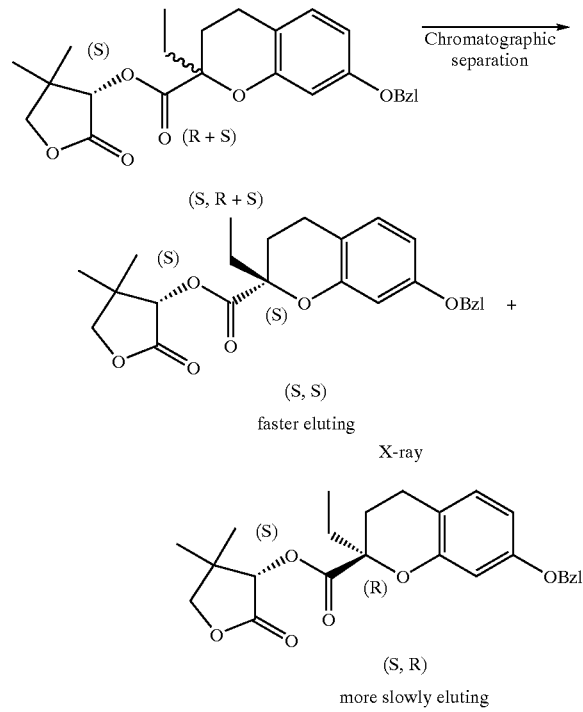

Following the procedure described above, the slower moving isomer was isolated when (S)-pantolactone was employed as a chiral auxiliary. This isomer was recrystallized from isopropanol-water to give prisms. Single crystal X-ray crystallographic analysis of this sample determined that the absolute stereochemistry of the 2-postion of chromane was (R) in relation to the known chiral center of (S)-pantolactone. This means that the slower moving isomer has (S, R) stereochemistry, and the faster isomer has (S, S) stereochemistry. Based on this data, and that enantiomers have the same physical properties except only optical rotation, it was concluded that when (R)-pantolactone was used, the slower moving isomer has (R, S) stereochemistry, and the faster eluting isomer has (R, R) stereochemistry.

(R, R) and (S, S) isomers: $^1$H-NMR (500 MHz, $CDCl_3$): δ 7.49 (m, 2H), 7.44 (m, 2H), 7.33 (m, 1H), 6.93 (d, 1H, J=8.5 Hz), 6.61 (d, 1H, J=2.5 Hz), 6.55 (dd, 1H, J=2.6, 8.4 Hz), 5.35 (s, 1H), 5.05 (s, 2H), 4.0 (s, 2H), 2.75 (m, 2H), 2.45 (m, 1H), 2.1 (m, 1H), 1.95 (m, 2H), 1.31 (t, 3H, J=7.5 Hz), 1.03 (s, 3H), 0.87 (s, 3H).

(R, S) and (S, R) isomers: $^1$H-NMR (500 MHz, $CDCl_3$): δ 7.44 (m, 2H), 7.39 (m, 2H), 7.33 (m, 1H), 6.93 (d, 1H, J=8.5 Hz), 6.59 (1H, J=2.5 Hz), 6.54 (dd, 1H, J=2.6, 8.4 Hz), 5.35 (s, 1H), 5.05 (s, 2H), 4.0 (s, 2H), 2.75 (m, 2H), 2.35 (m, 1H), 2.1 (m, 1H), 2.0 (m, 2H), 1.2 (s, 3H), 1.12 (t, 3H, J=7.5 Hz), 1.03 (s, 3H).

Solid-State Structure

The structure of the (S, R) ester has been determined by single crystal X-ray crystallography. Crystals suitable for diffraction studies were grown from a mixture of 2-propanol/water. The crystals obtained are monoclinic with space group $P2_1$ and cell constants of a=6.482(2), b=29.663 (7), c=11.097(3) Å, b=99.410(4)°, with V=2105(1) Å$^3$, and Z=4. The calculated density is 1.295 g cm$^{-3}$.

All diffraction measurements were made using monochromatized Mo $K_\alpha$ radiation ($\lambda$=0.71073 Å) on a CCD area-detector equipped diffractometer, at T=100 K, to a $\theta$ limit of 26.38°. There are 8568 unique reflections out of 22563 measured with 5238 observed at the I≧2σ(I) level. The structure was solved by direct methods and refined using full-matrix least-squares on $F^2$ using 595 parameters and all unique reflections. The refinement converged with agreement statistics of R=0.034, wR=0.052, S=0.76, $(\Delta/\sigma)_{max}$=5.43.

A computer-generated perspective view of the molecule is shown in FIG. 1. Lists of interatomic distances and angles are given in Tables 1 and 2, respectively.

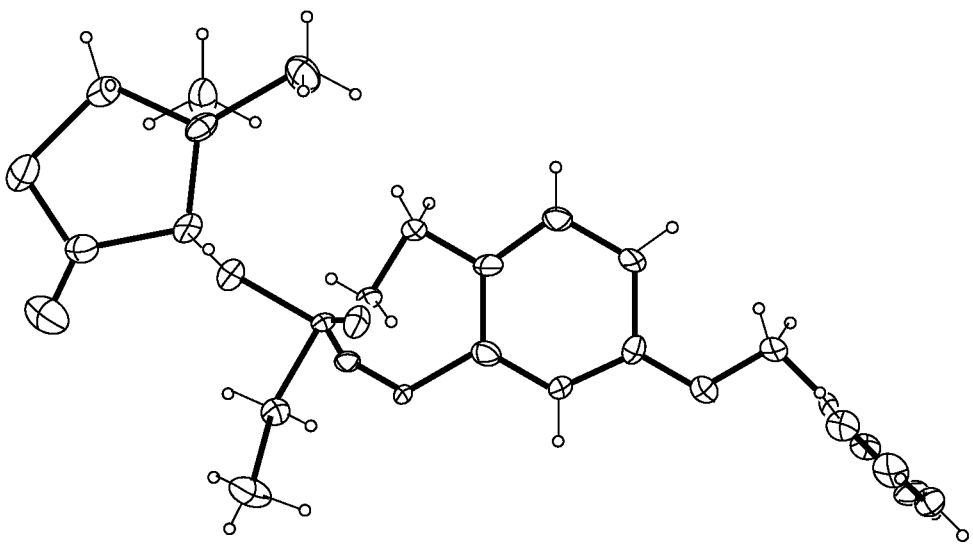

FIG. 1

TABLE 1

| Interatomic Distances (Å) | | | |
|---|---|---|---|
| O1–C9 | 1.391(2) | O31–C39 | 1.393(2) |
| O1–C2 | 1.453(2) | O31–C32 | 1.443(2) |
| O13–C12 | 1.201(2) | O43–C42 | 1.200(2) |
| O14–C12 | 1.357(2) | O44–C42 | 1.360(2) |
| O14–C15 | 1.444(2) | O44–C45 | 1.438(2) |
| O18–C19 | 1.348(2) | O48–C49 | 1.357(3) |
| O18–C17 | 1.471(2) | O48–C47 | 1.476(3) |
| O20–C19 | 1.202(2) | O50–C49 | 1.196(3) |
| O23–C7 | 1.384(2) | O53–C37 | 1.383(2) |
| O23–C24 | 1.458(2) | O53–C54 | 1.429(3) |
| C2–C11 | 1.506(3) | C32–C42 | 1.521(3) |
| C2–C12 | 1.528(3) | C32–C41 | 1.525(3) |
| C2–C3 | 1.535(3) | C32–C33 | 1.533(3) |
| C3–C4 | 1.530(3) | C33–C34 | 1.529(3) |
| C4–C10 | 1.516(3) | C34–C40 | 1.504(3) |
| C5–C10 | 1.389(3) | C35–C36 | 1.376(3) |
| C5–C6 | 1.397(3) | C35–C40 | 1.401(3) |
| C6–C7 | 1.384(3) | C36–C37 | 1.391(3) |
| C7–C8 | 1.389(3) | C37–C38 | 1.388(3) |
| C8–C9 | 1.376(3) | C38–C39 | 1.393(3) |
| C9–C10 | 1.396(3) | C39–C40 | 1.384(3) |
| C15–C19 | 1.511(3) | C45–C49 | 1.513(3) |
| C15–C16 | 1.529(3) | C45–C46 | 1.524(3) |
| C16–C22 | 1.525(3) | C46–C47 | 1.529(3) |
| C16–C17 | 1.530(3) | C46–C51 | 1.530(3) |
| C16–C21 | 1.533(3) | C46–C52 | 1.534(3) |
| C24–C25 | 1.506(3) | C54–C55 | 1.511(3) |

TABLE 1-continued

| Interatomic Distances (Å) | | | |
|---|---|---|---|
| C25–C30 | 1.384(3) | C55–C60 | 1.387(3) |
| C25–C26 | 1.389(3) | C55–C56 | 1.390(3) |
| C26–C27 | 1.387(3) | C56–C57 | 1.391(3) |
| C27–C28 | 1.378(3) | C57–C58 | 1.372(3) |
| C28–C29 | 1.390(3) | C58–C59 | 1.384(3) |
| C29–C30 | 1.393(3) | C59–C60 | 1.388(3) |

TABLE 2

| Interatomic Angles (deg.) | | | |
|---|---|---|---|
| C9–O1–C2 | 119.56(16) | C39–O31–C32 | 116.73(16) |
| C12–O14–C15 | 116.76(17) | C42–O44–C45 | 116.36(16) |
| C19–O18–C17 | 109.41(17) | C49–O48–C47 | 108.54(18) |
| C7–O23–C24 | 117.03(18) | C37–O53–C54 | 116.97(17) |
| O1–C2–C11 | 104.75(17) | O31–C32–C42 | 106.82(17) |
| O1–C2–C12 | 106.46(17) | O31–C32–C41 | 105.56(16) |
| C11–C2–C12 | 113.29(18) | C42–C32–C41 | 111.11(17) |
| O1–C2–C3 | 110.76(17) | O31–C32–C33 | 110.52(17) |
| C11–C2–C3 | 111.79(18) | C42–C32–C33 | 111.06(18) |
| C12–C2–C3 | 109.56(17) | C41–C32–C33 | 111.52(17) |
| C4–C3–C2 | 112.01(19) | C34–C33–C32 | 110.40(18) |
| C10–C4–C3 | 109.47(19) | C40–C34–C33 | 110.59(19) |
| C10–C5–C6 | 123.7(2) | C36–C35–C40 | 122.6(2) |
| C7–C6–C5 | 117.5(2) | C35–C36–C37 | 118.6(2) |
| O23–C7–C6 | 124.9(2) | O53–C37–C38 | 123.9(2) |
| O23–C7–C8 | 114.3(2) | O53–C37–C36 | 114.94(19) |
| C6–C7–C8 | 120.8(2) | C38–C37–C36 | 121.1(2) |
| C9–C8–C7 | 119.7(2) | C37–C38–C39 | 118.2(2) |
| C8–C9–O1 | 114.5(2) | C40–C39–O31 | 123.02(19) |
| C8–C9–C10 | 122.2(2) | C40–C39–C38 | 122.7(2) |
| O1–C9–C10 | 123.21(19) | O31–C39–C38 | 114.21(19) |
| C5–C10–C9 | 116.1(2) | C39–C40–C35 | 116.7(2) |
| C5–C10–C4 | 123.8(2) | C39–C40–C34 | 121.1(2) |
| C9–C10–C4 | 120.17(19) | C35–C40–C34 | 122.2(2) |
| O13–C12–O14 | 124.3(2) | O43–C42–O44 | 124.0(2) |
| O13–C12–C2 | 125.8(2) | O43–C42–C32 | 125.7(2) |
| O14–C12–C2 | 109.83(19) | O44–C42–C32 | 110.32(19) |

TABLE 2-continued

Interatomic Angles (deg.)

| | | | |
|---|---|---|---|
| O14–C15–C19 | 110.41(17) | O44–C45–C49 | 109.91(18) |
| O14–C15–C16 | 113.73(16) | O44–C45–C46 | 114.52(17) |
| C19–C15–C16 | 102.95(17) | C49–C45–C46 | 103.52(19) |
| C22–C16–C15 | 113.33(17) | C45–C46–C47 | 97.28(18) |
| C22–C16–C17 | 111.74(17) | C45–C46–C51 | 113.60(18) |
| C15–C16–C17 | 98.05(17) | C47–C46–C51 | 112.35(18) |
| C22–C16–C21 | 111.96(17) | C45–C46–C52 | 111.42(18) |
| C15–C16–C21 | 111.00(17) | C47–C46–C52 | 110.71(18) |
| C17–C16–C21 | 109.97(18) | C51–C46–C52 | 110.83(19) |
| O18–C17–C16 | 105.17(17) | O48–C47–C46 | 105.12(18) |
| O20–C19–O18 | 122.3(2) | O50–C49–O48 | 123.2(2) |
| O20–C19–C15 | 129.6(2) | O50–C49–C45 | 128.9(2) |
| O18–C19–C16 | 108.08(19) | O48–C49–C45 | 107.9(2) |
| O23–C24–C25 | 106.52(19) | O53–C54–C55 | 113.68(18) |
| C30–C25–C26 | 119.3(2) | C60–C55–C56 | 119.0(2) |
| C30–C25–C24 | 120.1(2) | C60–C55–C54 | 121.1(2) |
| C26–C25–C24 | 120.5(2) | C56–C55–C54 | 120.0(2) |
| C27–C26–C25 | 120.5(2) | C55–C56–C57 | 120.7(2) |
| C28–C27–C26 | 120.2(2) | C58–C57–C56 | 119.9(2) |
| C27–C28–C29 | 119.6(2) | C57–C58–C59 | 120.0(2) |
| C28–C29–C30 | 120.2(2) | C58–C59–C60 | 120.4(2) |
| C25–C30–C29 | 120.1(2) | C55–C60–C59 | 120.1(2) |

Step E: (2R)-Methyl 2-ethyl-7-hydroxychromane-2-carboxylate, and (2S)-Methyl 2-ethyl-7-hydroxychromane-2-carboxylate

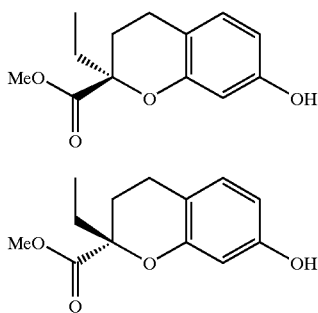

To a 250 ml, round-bottomed flask were added the (R, R) ester (5.07 g, 11.9 mmol) obtained as described in Step D, isopropanol 50 ml, and aqueous 2.5N sodium hydroxide 50 ml. This solution was heated to 65° C. overnight. Isopropanol was removed under reduced pressure, acidified to pH 1 with 2N hydrochloric acid, extracted with AcOEt three times. The combined organic layers were dried over anhydrous $Na_2SO_4$, filtered, and concentrated to give a thick oil.

This crude product was dissolved in dichloromethane and treated with diazomethane ethereal solution, concentrated, and chromatographed on silica gel eluting with 10 to 12.5% AcOEt/hexanes to give the corresponding methyl ester.

This methyl ester was dissolved in EtOH 200 ml and water 6 ml, and combined with 10% Pd/C 200 mg, placed in a Parr shaker and hydrogenated ($H_2$ 50 psi) overnight. The catalyst was removed by suction-filtration through a pad of celite. The filtrate was concentrated and chromatographed on silica gel using gradient elution 20 to 30% AcOEt/hexanes to gave the title compound 2.75 g (97%).

(2R)-Methyl 2-ethyl-7-hydroxychromane-2-carboxylate: $^1$H NMR (500 MHz, $CDCl_3$): δ 6.8 (d, 1H, J=8.2 Hz), 6.45 (d, 1H, J=2.6), 6.379 (dd, 1H, J=2.5, J=8.0 Hz), 3.728 (s, 3H), 2.593–2.655 (m, 2H), 2.327 (m, 1H), 1.993 (sext, 1H), 1.908 (m, 2H), 1.04 (t, 3H). ms: m/e=237 (M+1). $[\alpha]_D^{20}$+115.1 (c=1, MeOH)

In the same fashion, (2S)-Methyl 2-ethyl-7-hydroxychromane-2-carboxylate was prepared from the (R, S) isomer.

(2S)-Methyl 2-ethyl-7-hydroxychromane-2-carboxylate: $^1$H NMR (500 MHz, $CDCl_3$): δ 6.8 (d, 1H, J=8.2 Hz), 6.45 (d, 1H, J=2.6), 6.379 (dd, 1H, J=2.5, J=8.0 Hz), 3.728 (s, 3H), 2.593–2.655 (m, 2H), 2.327 (m, 1H), 1.993 (sext, 1H), 1.908 (m, 2H), 1.04 (t, 3H). ms: m/e=237 (M+1). $[\alpha]_D^{20}$−114.4 (c=1, MeOH)

Step F: (2R)-7-(3-(2-Chloro-4-phenoxyphenoxy)propoxy)-2-ethylchromane-2-carboxylic acid The title compound was prepared following the procedure described in Example 17, Steps B–C employing (2R)-methyl 2-ethyl-7-hydroxychromane-2-carboxylate (Example 25, Step E) instead of ethyl 7-hydroxychromane-2-carboxylate.

$^1$H-NMR (500 MHz, $CDCl_3$): δ 7.34 (m, 2H), 7.09 (m, 2H), 6.99–6.89 (m, 5H), 6.54 (d, 1H, J=2 Hz), 6.51 (dd, 1H, J=1.6, 8.2 Hz), 4.2 (t, 2H, J=6 Hz), 4.19 (t, 2H, J=5.9 Hz), 2.71 (m, 2H), 2.3 (m, 1H), 2.3 (p, 2H, J=6 Hz), 2.05–1.9 (m, 3H), 1.06 (t, 3H, J=7.4 Hz). ms: m/e=483 (M+1).

Example 26

(2R)-7-(3-(2-Chloro-4-(4-fluorophenoxy)phenoxy)propoxy)-2-ethylchromane-2-carboxylic acid

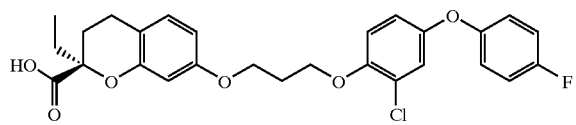

The title compound was prepared following the procedures described in Example 1, Steps B–C employing 3-bromopropyl 2-chloro-4-(4-fluorophenoxy)phenyl ether (Example 20, Step A) instead of 4-(3-bromopropoxy)-3-propylphenyl phenyl ether, and (2R)-methyl 2-ethyl-7-hydroxychromane-2-carboxylate (Example 25, Step E) instead of ethyl 7-hydroxychromane-2-carboxylate.

$^1$H-NMR (500 MHz, $CDCl_3$): δ 7.06–7.01 (m, 2H), 6.97–6.9 (m, 5H), 6.86 (dd, 1H, J=3, J=8.9 Hz), 6.55–6.51 (m, 2H), 4.2 (m, 4H), 2.7 (m, 2H), 2.3 (m 1H), 2.3 (p, 2H), J=6 Hz), 2.0 (m, 2H), 1.93 (m, 1H), 1.05 (t, 3H, J=7.3 Hz). ms: m/e=501 (M+1).

Example 27

(2S)-7-(3-(2-Chloro-4-phenoxyphenoxy)propoxy)-2-ethylchromane-2-carboxylic acid

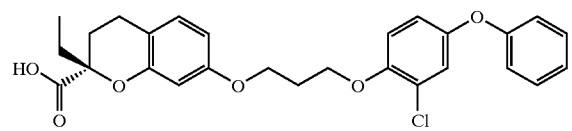

The title compound was prepared following the procedures described in Example 25 employing (2S)-methyl 2-ethyl-7-hydroxychromane-2-carboxylate (Example 25, Step E) instead of (2R)-methyl 2-ethyl-7-hydroxychromane-2-carboxylate.

$^1$H-NMR (500 MHz, $CDCl_3$): δ 7.34 (m, 2H), 7.09 (m, 2H), 6.99–6.89 (m, 5H), 6.54 (d, 1H, J=2 Hz), 6.51 (dd, 1H, J=1.6, 8.2 Hz), 4.2 (t, 2H, J=6 Hz), 4.19 (t, 2H, J=5.9 Hz), 2.71 (m, 2H), 2.3 (m, 1H), 2.3 (p, 2H, J=6 Hz), 2.05–1.9 (m, 3H), 1.06 (t, 3H, J=7.4 Hz). ms: m/e=483 (M+1).

Example 28

(2S)-7-(3-(2-Chloro-4-(4-fluorophenoxy)phenoxy)propoxy)-2-ethylchromane-2-carboxylic acid

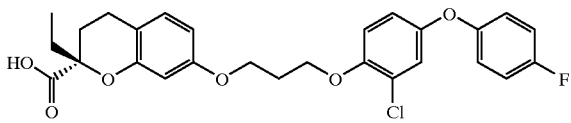

The title compound was prepared following the procedures described in Example 26 employing (2S)-methyl 2-ethyl-7-hydroxychromane-2-carboxylate (Example 25, Step E) instead of (2R)-methyl 2-ethyl-7-hydroxychromane-2-carboxylate.

$^1$H-NMR (500 MHz, CDCl$_3$): δ 7.05–7.01 (m, 2H), 6.97–6.9 (m, 5H), 6.86 (dd, 1H, J=3, J=8.9 Hz), 6.55–6.51 (m, 2H), 4.2 (m, 4H), 2.7 (m, 2H), 2.32 (m, 1H), 2.3 (p, 2H, J=6 Hz), 2.0 (m, 2H), 1.93 (m, 1H), 1.06 (t, 3H, J=7.3 Hz). ms: m/e=501 (M+1).

Example 29

(2R)-7-(3-(2-Propyl-4-(4-isobutylphenoxy)phenoxy)propoxy)-2-propylchromane-2-carboxylic acid

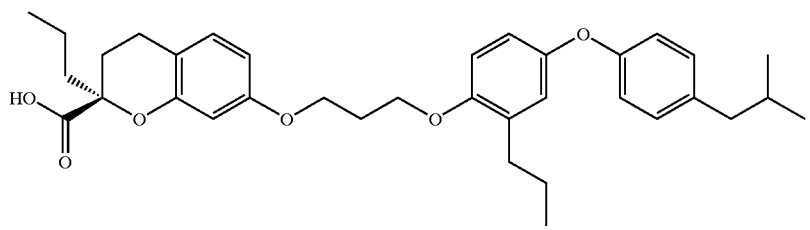

Step A: (2R)-Methyl-2-propyl-7-hydroxychromane-2-carboxylate, and (2S)-Methyl-2-propyl-7-hydroxychromane-2-carboxylate (R)

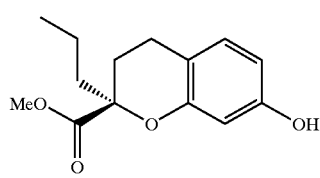

(S)

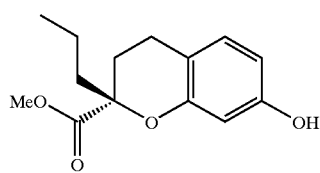

The title compounds were prepared following the procedures described in Example 25, Step A–E employing iodopropane instead of iodoethane.

(2R)-Methyl 2-propyl-7-hydroxychromane-2-carboxylate: $^1$H-NMR (500 MHz, CDCl$_3$): δ 6.85 (d, 1H, J=8.2 Hz), 6.45 (d, 1H, J=2.5 Hz), 6.35 (dd, J=2.5, 8.2 Hz), 4.95 (brs, 1H), 3.75 (s, 3H), 2.65 (m, 2H), 2.35 (m, 1H), 1.95 (m, 2H), 1.85 (m, 1H), 1.65 (m, 1H), 1.35 (m, 1H), 0.97 (t, 3H, J=7.4 Hz). ms: m/e=521 (M+1). [α]$_D^{20}$+102.8 (c=1, MeOH)

(2S)-Methyl 2-propyl-7-hydroxychromane-2-carboxylate: $^1$H-NMR (500 MHz, CDCl$_3$): δ 6.85 (d, 1H, J=8.2 Hz), 6.45 (d, 1H, J=2.5 Hz), 6.35 (dd, J=2.5, 8.2 Hz), 4.95 (brs, 1H), 3.75 (s, 3H), 2.65 (m, 2H), 2.35 (m, 1H), 1.95 (m, 2H), 1.85 (m, 1H), 1.65 (m, 1H), 1.35 (m, 1H), 0.97 (t, 3H, J=7.4 Hz). ms: m/e=251 (M+1). [α]$_D^{20}$−102.0 (c=1, MeOH).

Step B: (2R)-7-(3-(2-Propyl-4-(4-isobutylphenoxy)phenoxy)propoxy)-2-propylchromane-2-carboxylic acid The title compound was prepared following the procedures described in Example 17, Step B–C employing (2R)-methyl 2-propyl-7-hydroxychromane-2-carboxylate instead of ethyl 7-hydroxychromane-2-carboxylate, and 2-propyl-4-(4-isobutylphenoxy)phenol (U.S. Pat. No. 6,008,237) instead of 2-chloro-4-phenoxyphenol.

$^1$H-NMR (500 MHz, CDCl$_3$): δ 7.07 (d, 2H, J=8.5 Hz), 6.95 (d, 1H, J=8.3 Hz), 6.85 (d, 3H, J=8.2 Hz), 6.8 (s, 2H), 6.5 (m, 2H), 4.5 (t, 2H, J=6 Hz), 4.5 (t, 2H, J=6 Hz), 2.7 (m, 2H), 2.55 (t, 2H, J=7.1 Hz), 2.45 (d, 2H, J=7.1 Hz), 2.3 (m, 3H), 2.0–1.8 (m, 4H), 1.6 (m, 4H), 1.4 (m, 1H), 0.954 (m, 5H), 0.932 (s,3H), 0.919 (s, 3H). ms: m/e=561 (M+1).

What is claimed is:
1. A compound having the formula I:

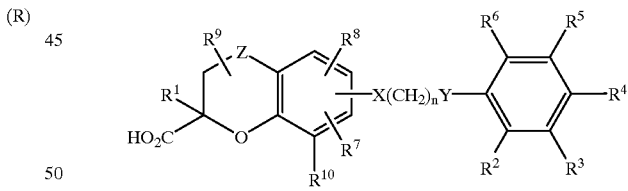

I or a pharmaceutically acceptable salt or prodrug thereof, wherein:

Z is selected from the group consisting of CH$_2$ and C═O;

R$^1$ is selected from the group consisting of H, —OH, C$_{1-7}$alkyl, C$_{2-7}$alkenyl, C$_{2-7}$alkynyl, —OC$_{1-3}$alkyl, —OC$_{2-3}$alkenyl, —OC$_{2-3}$alkynyl, F, Br, Cl, and Ar, wherein alkyl, alkenyl, alkynyl, —Oalkyl, —Oalkenyl and —Oalkynyl are linear or branched and are optionally substituted with (a) 1–7 halogen atoms, (b) 1–3 groups independently selected from (i) —OC$_{1-3}$alkyl, which is optionally substituted with 1–5 halogen atoms, and (ii) phenyl, which is optionally substituted with 1–3 groups independently selected from halogen, C$_{1-5}$alkyl and —OC$_{1-3}$alkyl, said C$_{1-5}$alkyl and —OC$_{1-3}$alkyl being linear or branched and optionally substituted with 1–5 halogens, or (c) a mixture of (a) and (b);

Ar is Aryl, wherein Aryl is in each instance optionally substituted with 1–5 substituents independently selected from (a) halogen, (b) $C_{1-5}$alkyl, (c) $C_{2-5}$alkenyl, (d) $C_{2-5}$alkynyl, (e) —$OC_{1-5}$alkyl, (f) —$OC_{2-5}$alkenyl, (g) —$OC_{2-5}$alkynyl, (h) —$SO_xC_{1-5}$alkyl, (i) —$SO_xNR^aR^b$, (j) —$SO_x$phenyl, (k) —C(O)$C_{1-3}$alkyl, and (l) —C(O)$NR^aR^b$, wherein in each instance, each alkyl, alkenyl and alkynyl is linear or branched and is optionally substituted with (a) 1–5 halogen atoms, (b) 1–2 groups independently selected from —$OC_{1-3}$alkyl, which is linear or branched and is optionally substituted with 1–5 halogens, or (c) a mixture thereof, and wherein phenyl is optionally substituted with 1–3 substituents independently selected from halogen, $C_{1-3}$alkyl, and $C_{1-3}$alkoxy, wherein $C_{1-3}$alkyl and $C_{1-3}$alkoxy are linear or branched and are optionally substituted with 1–5 halogens;

x is selected from 0, 1 and 2;

Aryl is selected from phenyl and naphthyl;

$R^a$ and $R^b$ are independently selected from the group consisting of H, $C_{1-5}$alkyl, $C_{2-5}$alkenyl, $C_{2-5}$alkynyl, —C(O)$C_{1-5}$alkyl, —C(O)$C_{2-5}$alkenyl, —C(O)$C_{2-5}$alkynyl, $SO_xC_{1-5}$alkyl, $SO_x$phenyl, $SO_xNR^dR^e$, —C(O)$NR^dR^e$, halogen, and phenyl, wherein in all instances, alkyl, alkenyl, and alkynyl are linear or branched and are optionally substituted with (a) 1–5 halogen atoms, (b) 1–3 groups independently selected from —$OCH_3$, —$OCF_3$ and phenyl, or (c) a mixture thereof, wherein phenyl in all occurrences is optionally substituted with 1–3 substituents independently selected from halogen, $C_{1-3}$alkyl, and $C_{1-3}$alkoxy, said $C_{1-3}$alkyl and $C_{1-3}$alkoxy being linear or branched and optionally substituted with 1–5 halogens;

$R^d$ and $R^e$ are independently selected from H, $C_{1-5}$alkyl, $C_{2-5}$alkenyl, $C_{2-5}$alkynyl, and phenyl, wherein said alkyl, alkenyl, and alkynyl are linear or branched and are optionally substituted with (a) 1–5 halogen atoms, (b) 1–3 groups independently selected from —$OCH_3$, —$OCF_3$ and phenyl, or (c) a mixture thereof, wherein phenyl in all occurrences is optionally substituted with 1–3 substituents independently selected from halogen, $C_{1-3}$alkyl, and $C_{1-3}$alkoxy, said $C_{1-3}$alkyl and $C_{1-3}$alkoxy being linear or branched and optionally substituted with 1–5 halogens;

X and Y are independently selected from the group consisting of O, S, SO, $SO_2$, $NR^a$ and $CH_2$;

n is an integer from 1–6;

$R^2$, $R^3$, $R^5$, $R^6$, $R^7$, $R^8$, $R^9$ and $R^{10}$ are independently selected from the group consisting of H, halogen, $C_{1-7}$alkyl, $C_{2-7}$alkenyl, $C_{2-7}$alkynyl, —OH, —$OC_{1-5}$alkyl, —$OC_{2-5}$alkenyl, —$OC_{2-5}$alkynyl, —C(O)$C_{1-5}$alkyl, —C(O)$C_{2-5}$alkenyl, —C(O)$C_{2-5}$alkynyl, —C(O)$OC_{1-5}$alkyl, —C(O)$OC_{2-5}$alkenyl, —C(O)$OC_{2-5}$alkynyl, —OC(O)$C_{1-5}$alkyl, —OC(O)$C_{2-5}$alkenyl, Ar, —OAr, —C(O)Ar, —C(O)OAr, —OC(O)Ar, $C_{3-8}$Cycloalkyl, —$OC_{3-8}$Cycloalkyl, —$SO_xC_{1-5}$alkyl, —$SO_xNR^aR^b$, —$SO_x$Ar, and —C(O)$NR^aR^b$, wherein in each instance, each alkyl, alkenyl, and alkynyl is linear or branched and is optionally substituted with (a) 1–5 halogen atoms, (b) 1–2 groups independently selected from —$OC_{1-3}$alkyl groups which are linear or branched and are optionally substituted with 1–5 halogens, (c) 1 group Ar or $C_{3-6}$Cycloalkyl, or (d) a mixture of more than one of (a), (b) and (c); and $R^4$ is OAr.

2. A compound having formula I as recited in claim 1, wherein X and Y are each O or S.

3. A compound having formula I as recited in claim 1, wherein X and Y are O.

4. A compound having formula I as recited in claim 1, wherein Z is $CH_2$.

5. A compound having formula I as recited in claim 1, wherein Z is C=O.

6. A compound having formula I as recited in claim 1, wherein n is 3 or 4.

7. A compound having formula I as recited in claim 1, wherein $R^1$ is selected from the group consisting of Cl, Br, F and $C_{1-4}$alkyl, wherein said $C_{1-4}$alkyl is linear or branched and is optionally substituted with 1–3 halogens independently selected from F and Cl, 1 phenyl which is optionally substituted with 1–3 halogens, or a mixture thereof.

8. A compound having formula I as recited in claim 1, wherein $R^2$ is selected from the group consisting of Cl, Br, F and $C_{1-4}$alkyl, wherein said $C_{1-4}$alkyl is optionally substituted with 1–3 halogens.

9. A compound having formula I as recited in claim 1, wherein the group —X— is attached to the benzopyran ring at the 6-position of the benzopyran ring.

10. A compound having formula I as recited in claim 1, wherein the group —X— is attached to the benzopyran ring at the 7-position of the benzopyran ring.

11. A compound having formula I as recited in claim 1, wherein $R^1$ is selected from a group consisting of $C_{1-4}$alkyl, Cl and F, wherein alkyl is linear or branched and is optionally substituted with 1–5 F.

12. A compound as recited in claim 1, wherein Ar is phenyl, which is optionally substituted with 1–4 groups independently selected from Cl, F, $C_{1-5}$alkyl, —$OCH_3$, —$OCF_3$, —$SO_xC_{1-5}$alkyl, —$SO_xNR_aR_b$, —$SO_x$phenyl, —C(O)$C_{1-3}$alkyl, and —C(O)$NR^aR^b$, wherein phenyl of —$O_x$phenyl is optionally substituted with 1–3 substituents independently selected from halogen, $CH_3$, $CF_3$, —$OCF_3$, and —$OCH_3$, and wherein alkyl in all occurrences is linear or branched and is optionally substituted with 1–5 halogens.

13. A compound as recited in claim 12, wherein $R^1$ and $R^2$ are each independently selected from a group consisting of $C_{1-4}$alkyl, Cl and F; n is 2–4; X and Y are O; Z is $CH_2$; $R^3$, $R^5$, $R^6$, $R^7$, $R^8$, $R^9$ and $R^{10}$ are independently selected from H, Cl, F, $CH_3$ and $CF_3$; and in all occurrences, alkyl is linear or branched and is optionally substituted with 1–5 F.

14. A compound having formula I as recited in claim 1, wherein $R^3$, $R^5$, $R^6$, $R^7$, $R^8$, $R^9$, and $R^{10}$ are H; $R^2$ is Cl or F; and $R^1$ is $C_{1-4}$alkyl, Cl or F, where $C_{1-4}$alkyl is linear or branched and is optionally substituted with 1–5 F.

15. A compound having formula I as recited in claim 1, wherein $R^3$, $R^5$ and $R^6$ are H.

16. A compound as recited in claim 1, wherein $R^a$ and $R^b$ are independently selected from the group consisting of H, $C_{1-5}$alkyl, —C(O)$C_{1-5}$alkyl, $S(O)_xC_{1-5}$alkyl, $S(O)_x$phenyl, and phenyl, wherein alkyl in all occurrences is linear or branched and is optionally substituted with 1–5 halogen atoms, and wherein phenyl in all occurrences is optionally substituted with 1–3 substituents independently selected from halogen, $C_{1-3}$alkyl, and $C_{1-3}$alkoxy, wherein $C_{1-3}$alkyl and $C_{1-3}$alkoxy are linear or branched and are optionally substituted with 1–5 halogens.

17. A compound as recited in claim 1, wherein $R^1$ is not H or —$CR^{11}R^{12}$—, and no more than one of $R^2$, $R^6$, and $R^{10}$ is alkyl.

18. A compound as recited in claim 1, wherein $R^2$ is Cl, Br or F, and $R^{10}$ is not alkyl.

19. A compound as recited in claim 13, wherein $R^3$, $R^5$, $R^6$, $R^7$, $R^8$, $R^9$ and $R^{10}$ are H.

20. A compound having formula Ia:

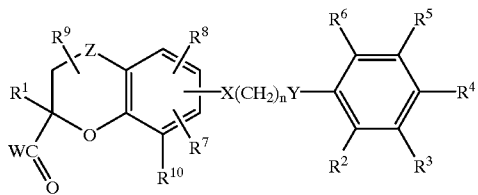

or a pharmaceutically acceptable salt or metabolite thereof, wherein W is a group that is easily removed under physiological conditions during or after administration to a mammalian patient to yield a carboxylic acid in which W is OH, or the carboxylate anion thereof, or a pharmaceutically acceptable salt thereof, and $R^1$, $R^2$, $R^3$, $R^4$, $R^5$, $R^6$, $R^7$, $R^8$, $R^9$, $R^{10}$, $R^{11}$, $R^{12}$, Ar, X, Y, Z, $R^a$, $R^b$, $R^c$, $R^d$, $R^e$, x and n are as defined in claim 1.

21. A compound as recited in claim 20, wherein W is selected from the group consisting of $-OR^{13}$, $-OCH_2OR^{13}$, $-OCH(CH_3)OR^{13}$, $-OCH_2OC(O)R^{13}$, $-OCH(CH_3)OC(O)R^{13}$, $-OCH_2OC(O)OR^{13}$, $-OCH(CH_3)OC(O)OR^{13}$, and $-NR^{14}R^{14}$, wherein each $R^{13}$ is independently selected from $C_1$–$C_6$ alkyl optionally substituted with one or two groups independently selected from $-CO_2H$, $-CONH_2$, $NH_2$, $-OH$, $-OAc$, NHAc and phenyl; and wherein each $R^{14}$ is independently selected from H and $R^{13}$.

22. A compound as recited in claim 1, wherein the stereochemistry at the 2-position of the benzopyranyl ring is R.

23. A compound as recited in claim 1, wherein the stereochemistry at the 2-position of the benzopyranyl ring is S.

24. A compound represented by a structure shown below, or a pharmaceutically acceptable salt or prodrug thereof, wherein the structure is selected from the group consisting of:

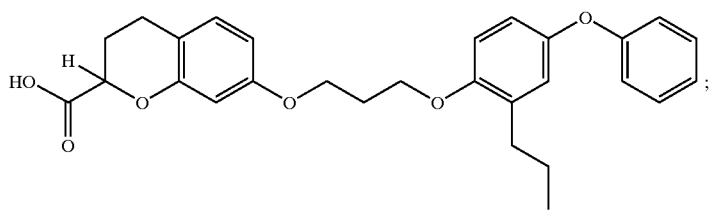

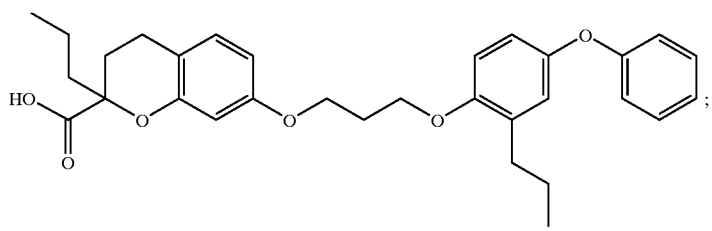

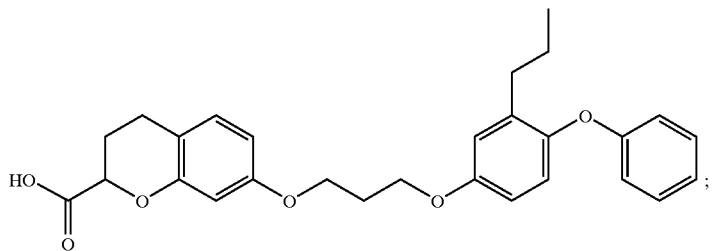

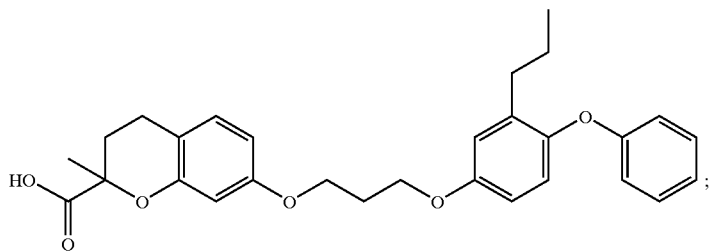

-continued
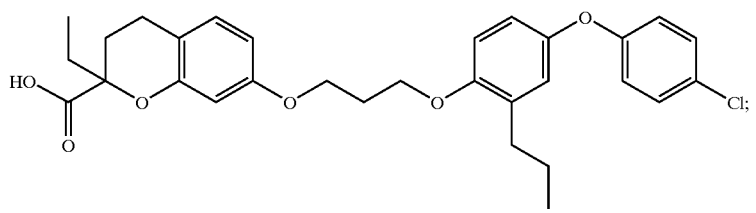
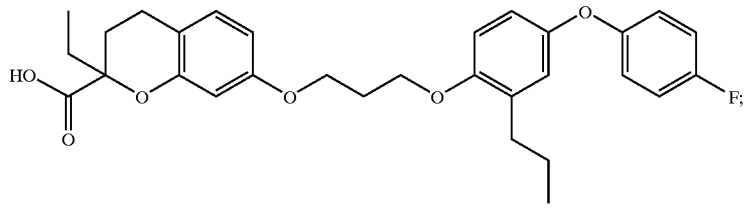
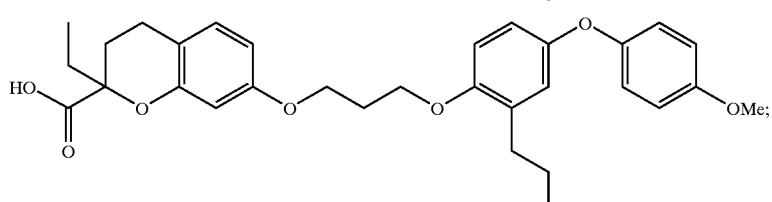
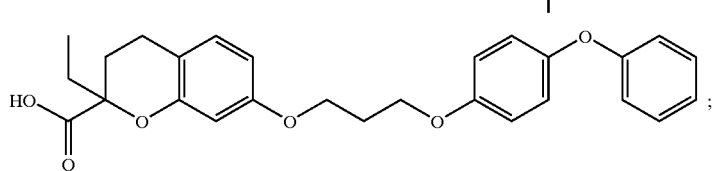
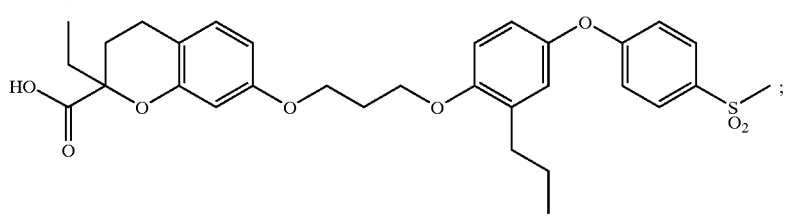
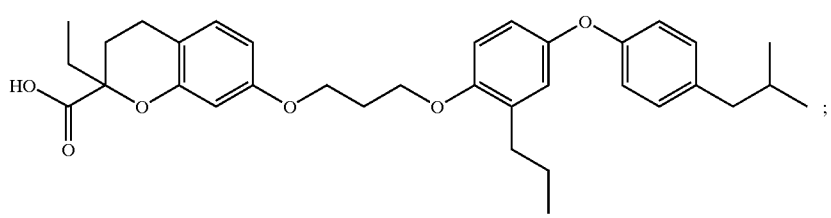
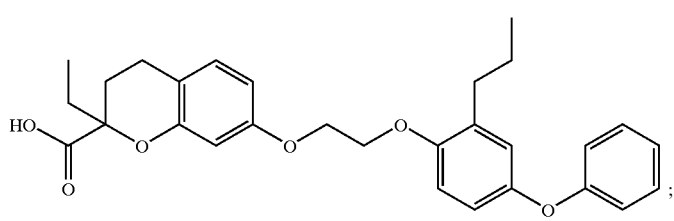
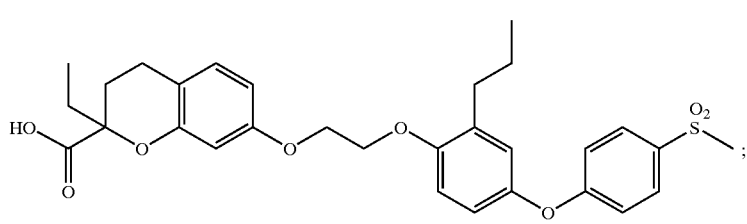

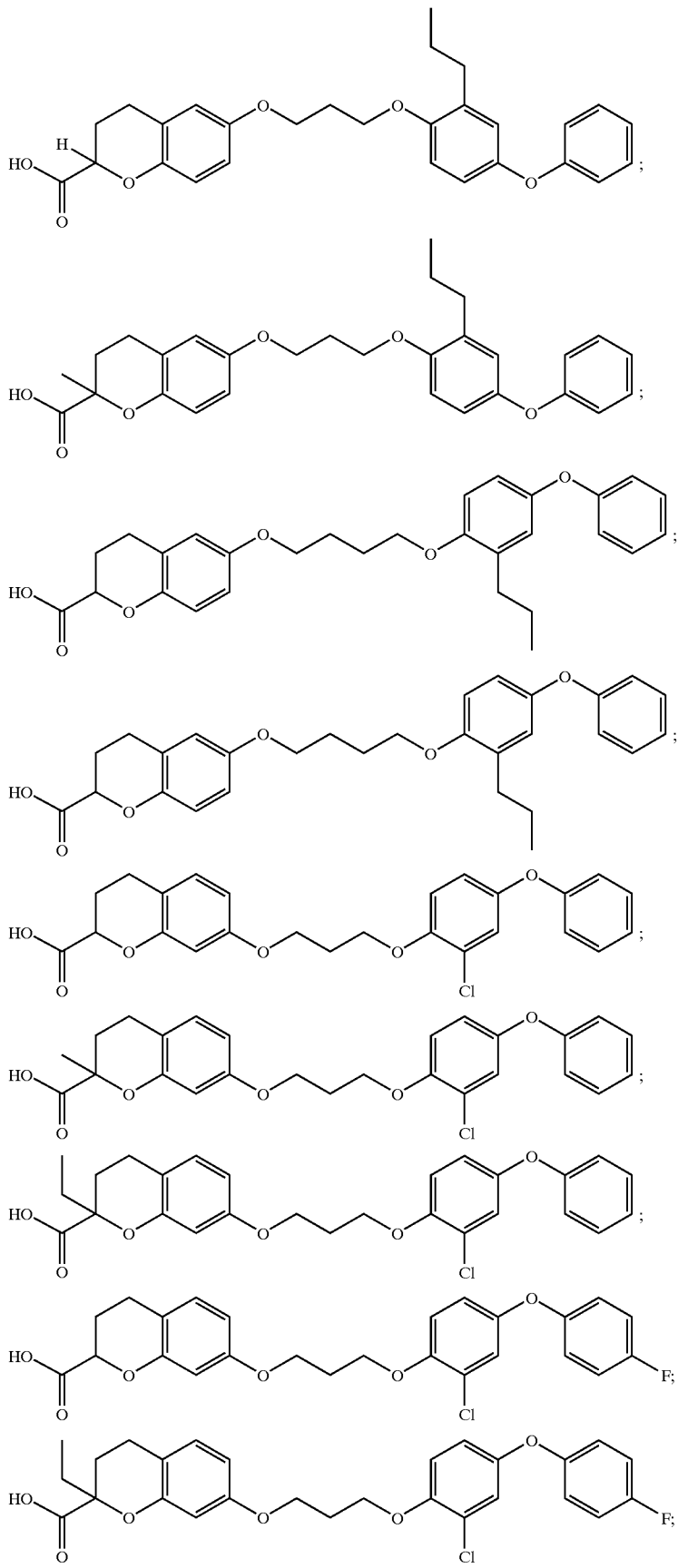

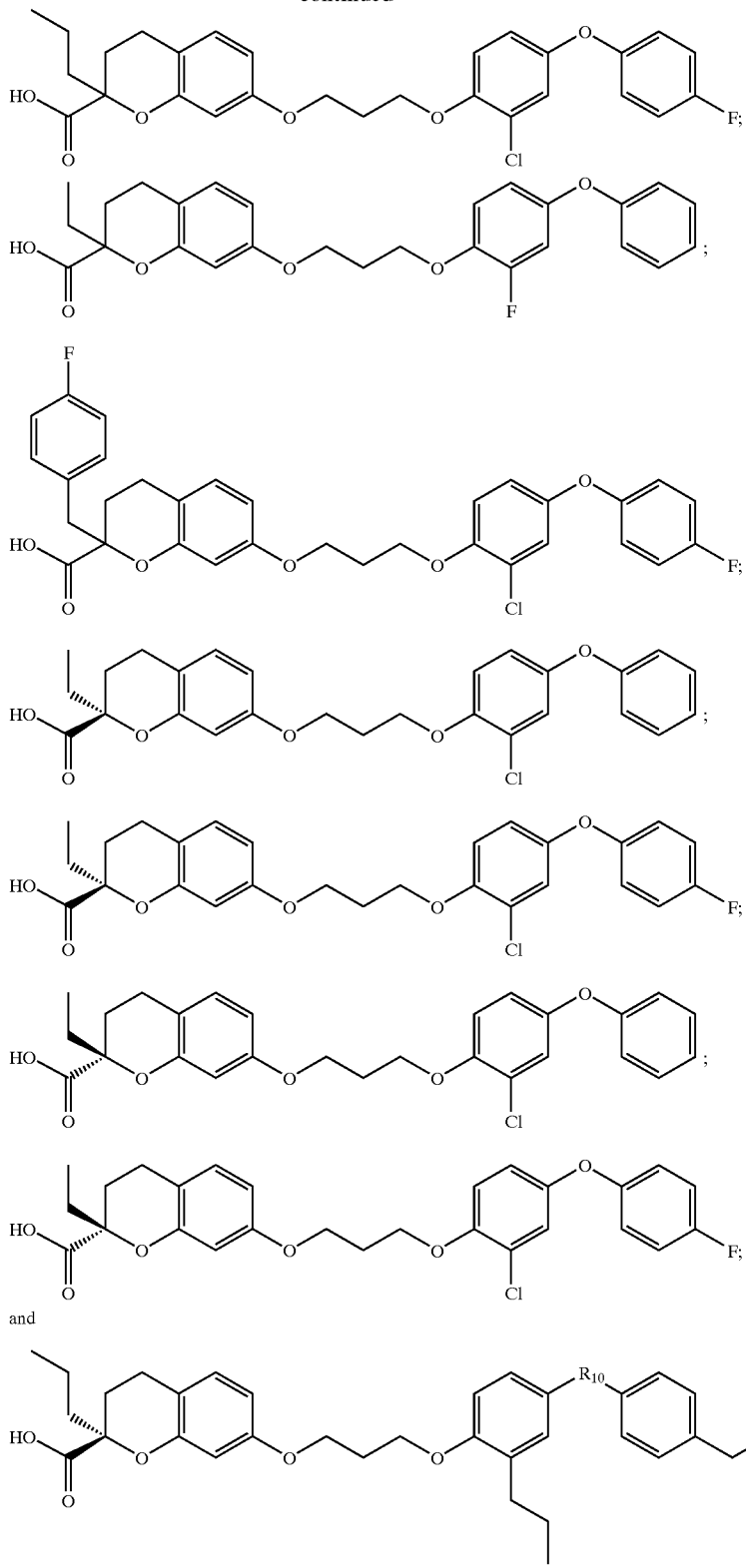

and

25. A pharmaceutical composition comprising a compound as identified in claim 1 and a pharmaceutically acceptable carrier.

26. A method for treating or controlling non-insulin dependent (Type 2) diabetes mellitus in a mammalian patient in need of such treatment which comprises administering to said patient a therapeutically effective amount of a compound of claim 1.

27. A method for treating or controlling hyperglycemia in a mammalian patient in need of such treatment which comprises administering to said patient a therapeutically effective amount of a compound of claim 1.

28. A method for treating, controlling or preventing lipid disorders, hyperlipidemia, or low HDL in a mammalian patient in need of such treatment which comprises administering to said patient a therapeutically effective amount of a compound of claim 1.

29. A method for treating, controlling or preventing obesity in a mammalian patient in need of such treatment which comprises administering to said patient a therapeutically effective amount of a compound of claim 1.

30. A method for treating, controlling or preventing hypercholesterolemia in a mammalian patient in need of such treatment which comprises administering to said patient a therapeutically effective amount of a compound of claim 1.

31. A method for treating, controlling or preventing hypertriglyceridemia in a mammalian patient in need of such treatment which comprises administering to said patient a therapeutically effective amount of a compound of claim 1.

32. A method for treating, controlling or preventing dyslipidemia and/or low HDL cholesterol in a mammalian patient in need of such treatment which comprises administering to said patient a therapeutically effective amount of a compound of claim 1.

33. A method for treating or controlling atherosclerosis in a mammalian patient in need of such treatment which comprises administering to said patient a therapeutically effective amount of a compound of claim 1.

34. A method for treating, controlling or preventing cachexia in a mammalian patient in need of such treatment which comprises administering to said patient a therapeutically effective amount of a compound of claim 1.

35. A method of treating or controlling one or more diseases, disorders, or conditions selected from the group consisting of (1) non-insulin dependent diabetes mellitus (NIDDM), (2) hyperglycemia, (3) impaired glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) irritable bowel syndrome, (16) inflammatory bowel disease, including Crohn's disease and ulcerative colitis, (17) other inflammatory conditions, (18) pancreatitis, (19) abdominal obesity, (20) neurodegenerative disease, (21) retinopathy, (22) neoplastic conditions, (23) adipose cell tumors, (24) adipose cell carcinomas, such as liposarcoma, (25) prostate cancer and other cancers, including gastric, breast, bladder and colon cancers, (26) angiogenesis, (27) Alzheimer's disease, (28) psoriasis, (29) acne vulgaris, (30 skin diseases modulated by PPAR, (31) high blood pressure, (32) Syndrome X, (33) ovarian hyperandrogenism (polycystic ovarian syndrome), and other disorders where insulin resistance is a component, said method comprising the administration of an effective amount of a compound of claim 1.

36. A method of treating or controlling one or more diseases, disorders, or conditions selected from the group consisting of (1) diabetes mellitus, and especially non-insulin dependent diabetes mellitus (NIDDM), (2) hyperglycemia, (3) impaired glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) irritable bowel syndrome, (16) inflammatory bowel disease, including Crohn's disease and ulcerative colitis, (17) other inflammatory conditions, (18) pancreatitis, (19) abdominal obesity, (20) neurodegenerative disease, (21) retinopathy, (22) neoplastic conditions, (23) adipose cell tumors, (24) adipose cell carcinomas, such as liposarcoma, (25) prostate cancer and other cancers, including gastric, breast, bladder and colon cancers, (26) angiogenesis, (27) Alzheimer's disease, (28) psoriasis, (29) acne vulgaris, (30) skin diseases modulated by PPAR, (31) high blood pressure, (32) Syndrome X, (33) ovarian hyperandrogenism (polycystic ovarian syndrome), and other disorders where insulin resistance is a component, said method comprising the administration of an effective amount of a compound of claim 1, and an effective amount of one or more other compounds selected from the group consisting of:

(a) insulin sensitizers; (ii) biguanides; (iii) protein tyrosine phosphatase-1B (PTP-1B) inhibitors; and (iv) dipeptidyl peptidase IV inhibitors;

(b) insulin or insulin mimetics;

(c) sulfonylureas;

(d) α-glucosidase inhibitors;

(e) cholesterol lowering agents selected from the group consisting of (I) HMG-CoA reductase inhibitors, (ii) sequestrants, (iii) nicotinyl alcohol, nicotinic acid or a salt thereof, (iv) PPARα agonists, (v) PPARα/γ dual agonists, (vi) inhibitors of cholesterol absorption, (vii) acyl CoA:cholesterol acyltransferase inhibitors, and (Viii) anti-oxidants;

(f) PPARδ agonists;

(g) antiobesity compounds (anorectics);

(h) an ileal bile acid transporter inhibitor; and (i) anti-inflammatory agents.

37. A method for the treatment, control, or prevention of one or more conditions selected from hypercholesterolemia, atherosclerosis, low HDL levels, high LDL levels, hyperlipidemia, hypertriglyceridemia, and dyslipidemia, which method comprises administering to a mammalian patient in need of such treatment a therapeutically effective amount of a compound of claim 1 and a therapeutically effective amount of an HMG-CoA reductase inhibitor.

38. The method as recited in claim 37, wherein the HMG-CoA reductase inhibitor is a statin.

39. The method as recited in claim 38, wherein the statin is selected from the group consisting of lovastatin, simvastatin, pravastatin, fluvastatin, atorvastatin, itavastatin, rosuvastatin and rivastatin.

40. A method for the treatment, control, or prevention of one or more conditions selected from inflammatory conditions, inflammatory bowel disease, Crohn's disease, and ulcerative colitis, which method comprises administering to a mammalian patient in need of such treatment a therapeutically effective amount of a compound according to claim 1.

41. A method for treating or controlling atherosclerosis in a mammalian patient in need of such treatment comprising the administration to said patient of an effective amount of a compound of claim 1 and an effective amount of an HMG-CoA reductase inhibitor.

42. The method as recited in claim 41, wherein the HMG-CoA reductase inhibitor is a statin.

43. The method as recited in claim 42, wherein the statin is selected from the group consisting of lovastatin, simvastatin, pravastatin, fluvastatin, atorvastatin, itavastatin, rosuvastatin and rivastatin.

44. A pharmaceutical composition, comprising: (1) a compound according to claim 1, (2) an HMG-CoA reductase inhibitor, and (3) a pharmaceutically acceptable carrier.

45. A pharmaceutical composition comprising (1) a compound according to claim 1, (2) one or more compounds selected from the group consisting of:
- (a) insulin sensitizers; (ii) biguanides; (iii) protein tyrosine phosphatase-1B (PTP-1B) inhibitors; and (iv) dipeptidyl peptidase IV (DP-IV) inhibitors;
- (b) insulin or insulin mimetics;
- (c) sulfonylureas;
- (d) α-glucosidase inhibitors;
- (e) cholesterol lowering agents selected from the group consisting of (i) HMG-CoA reductase inhibitors, (ii) sequestrants, (iii) nicotinyl alcohol, nicotinic acid or a salt thereof, (iv) PPARα agonists, (v) PPARα/γ dual agonists, (vi) inhibitors of cholesterol absorption, (vii) acyl CoA:cholesterol acyltransferase inhibitors, and (viii) anti-oxidants;
- (f) PPARδ agonists;
- (g) antiobesity compounds (anorectics);
- (h) an ileal bile acid transporter inhibitor; and
- (i) anti-inflammatory agents; and (3) a pharmaceutically acceptable carrier.

* * * * *